US008394760B2

(12) United States Patent
Yang et al.

(10) Patent No.: US 8,394,760 B2
(45) Date of Patent: *Mar. 12, 2013

(54) MULTIFUNCTIONAL NANOSTRUCTURES, METHODS OF SYNTHESIZING THEREOF, AND METHODS OF USE THEREOF

(75) Inventors: Lily Yang, Decatur, GA (US); Shuming Nie, Atlanta, GA (US); Xiaohu Gao, Shoreline, WA (US); Xiang Hong Peng, Stone Mountain, GA (US)

(73) Assignee: Emory University, Atlanta, GA (US)

( * ) Notice: Subject to any disclaimer, the term of this patent is extended or adjusted under 35 U.S.C. 154(b) by 1019 days.

This patent is subject to a terminal disclaimer.

(21) Appl. No.: 11/919,681

(22) PCT Filed: May 2, 2006

(86) PCT No.: PCT/US2006/016880
§ 371 (c)(1),
(2), (4) Date: Nov. 21, 2008

(87) PCT Pub. No.: WO2007/018647
PCT Pub. Date: Feb. 15, 2007

(65) Prior Publication Data
US 2009/0123365 A1 May 14, 2009

Related U.S. Application Data

(60) Provisional application No. 60/676,812, filed on May 2, 2005.

(51) Int. Cl.
*C07K 14/00* (2006.01)
(52) U.S. Cl. .......... 514/2; 977/705; 977/733; 423/414
(58) Field of Classification Search .............. None
See application file for complete search history.

(56) References Cited

U.S. PATENT DOCUMENTS

| 7,217,457 B2 * | 5/2007 | Elaissari et al. ............ 428/407 |
| 7,846,412 B2 * | 12/2010 | Nie et al. .................. 423/414 |
| 2009/0196831 A1 * | 8/2009 | Yang et al. ................ 424/9.322 |

OTHER PUBLICATIONS

Kumar NA, Schnall MD. MR imaging: its current and potential utility in the diagnosis and management of breast cancer. Magn Reson Imaging Clin N Am 2000;8:715-28.
Bombardieri E, Crippa F. PET imaging in breast cancer. Q J Nucl Med 2001;45:245-56.
Aziz SA, Pervez S, Khan S, Kayani N, Rahbar MH. Epidermal growth factor receptor (EGFR) as a prognostic marker: an immunohistochemical study on 315 consecutive breast carcinoma patients. J Pak Med Assoc 2002;52:104-10.
Albanell J, Codony J, Rovira A, Mellado B, Gascon P. Mechanism of action of anti-HER2 monoclonal antibodies: scientific update on trastuzumab and 2C4. Adv Exp Med Biol 2003;532:253-68.
Bruell D, Bruns CJ, Yezhelyev M, Huhn M, Muller J, Ischenko I, Fischer R, Finnern R, Jauch KW, Barth S. Recombinant anti-EGFR immunotoxin 425(scFv)-ETA demonstrates anti-tumor activity against disseminated human pancreatic cancer in nude mice. Int J Mol Med 200515:305-13.
Jannot CB, Beerli RR, Mason S, Gullick WJ, Hynes NE. Intracellular expression of a single-chain antibody directed to the EGFR leads to growth inhibition of tumor cells. Oncogene 1996;13:275-82.
Josephson L, Kircher MF, Mahmood U, Tang Y, Weissleder R. Near-infrared fluorescent nanoparticles as combined MR/optical imaging probes. Bioconjug Chem 2002;13:554-60.
Li Y, Wood N, Yellowlees D, Donnelly PK. Cell surface expression of urokinase receptor in normal mammary epithelial cells and breast cancer cell lines. Anticancer Res 1999;19:1223-8.
Adams GP, Schier R, McCall AM, Simmons HH, Horak EM, Alpaugh RK, Marks JD, Weiner LM. High affinity restricts the localization and tumor penetration of single-chain fv antibody molecules. Cancer Res 2001;61:4750-5.
Akerman ME, Chan WC, Laakkonen P, Bhatia SN, Ruoslahti E. Nanocrystal targeting in vivo. Proc Natl Acad Sci U S A 2002;99:12617-21.
Arap W, Haedicke W, Bernasconi M, Kain R, Rajotte D, Krajewski S, Ellerby HM, Bredesen DE, Pasqualini R, Ruoslahti E. Targeting the prostate for destruction through a vascular address. Proc Natl Acad Sci U S A 2002;99:1527-31.
Arbiser JL, Bingaman A, Durham M, Cowan S, Cohen C, Zarnegar E, Varma V, Larsen CP. SVR angiosarcomas can be rejected by CD4 costimulation dependent and CD8 costimulation independent pathways. Mol Med 2002;8:551-8.
Arteaga CL, Baselga J. Tyrosine kinase inhibitors: why does the current process of clinical development not apply to them? Cancer Cell 2004;5:525-31.
Arteaga CL, Truica CI. Challenges in the development of anti-epidermal growth factor receptor therapies in breast cancer. Semin Oncol 2004;31:3-8.
Artemov D, Mori N, Okollie B, Bhujwalla ZM. MR molecular imaging of the Her-2/neu receptor in breast cancer cells using targeted iron oxide nanoparticles. Magn Reson Med 2003;49:403-8.
Artemov D, Mori N, Ravi R, Bhujwalla ZM. Magnetic resonance molecular imaging of the HER-2/neu receptor. Cancer Res 2003;63:2723-7.
Aslakson CJ, Miller FR. Selective events in the metastatic process defined by analysis of the sequential dissemination of subpopulations of a mouse mammary tumor. Cancer Res 1992;52:1399-405.
Bailey RE, Nie S. Alloyed semiconductor quantum dots: tuning the optical properties without changing the particle size. J Am Chem Soc 2003;125:7100-6.
Bander NH, Trabulsi EJ, Kostakoglu L, Yao D, Vallabhajosula S, Smith-Jones P, Joyce MA, Milowsky M, Nanus DM, Goldsmith SJ. Targeting metastatic prostate cancer with radiolabeled monoclonal antibody J591 to the extracellular domain of prostate specific membrane antigen. J Urol 2003;170:1717-21.
Behrendt N. The urokinase receptor (uPAR) and the uPAR-associated protein (uPARAP/Endo180): membrane proteins engaged in matrix turnover during tissue remodeling. Biol Chem 2004;385:103-36.
Brannon-Peppas L, Blanchette JO. Nanoparticle and targeted systems for cancer therapy. Adv Drug Deliv Rev 2004;56:1649-59.
Brigger I, Dubernet C, Couvreur P. Nanoparticles in cancer therapy and diagnosis. Adv Drug Deliv Rev 2002;54:631-51.

(Continued)

*Primary Examiner* — Anand Desai
(74) *Attorney, Agent, or Firm* — Morris Manning & Martin LLP; Tim Tingkang Xia, Esq.

(57) ABSTRACT

A nanostructure and methods of synthesizing same. In one embodiment, the nanostructure includes a nanospecies, a hydrophobic protection structure including at least one compound selected from a capping ligand, an amphiphilic copolymer, and combinations thereof, wherein the hydrophobic protection structure encapsulates the nanospecies, and at least one histidine-tagged peptide or protein conjugated to the hydrophobic protection structure, wherein the at least one histidine-tagged peptide or protein has at least one binding site.

20 Claims, 13 Drawing Sheets

OTHER PUBLICATIONS

Bulte J.W., Iron Oxide MR Contrast Agents for Molecular and Cellular Imaging. NMR Biomed. 2004;17:484-499.
Carriero MV, Del Vecchio S, Capozzoli M, Franco P, Fontana L, Zannetti A, Botti G, D'Aiuto G, Salvatore M, Stoppelli MP. Urokinase receptor interacts with alpha(v)beta5 vitronectin receptor, promoting urokinase-dependent cell migration in breast cancer. Cancer Res 1999;59:5307-14.
Chan et al., Luminescent Quantum Dots for Multiplexed Biological Detection and Imaging, Current Opinion in Biotechnology, 2002, vol. 13, pp. 40-46.
Chen X, Conti PS, Moats RA. In vivo near-infrared fluorescence imaging of integrin alphavbeta3 in brain tumor xenografts. Cancer Res 2004;64:8009-14.
Dancey J.E., Predictive factors for epidermal growth factor receptor inhibitors—the bull's-eye hits the arrow. Cancer Cell 2004;5:411-5.
Dear AE, Medcalf RL. The urokinase-type-plasminogen-activator receptor (CD87) is a pleiotropic molecule. Eur J Biochem 1998;252:185-93.
Derfus, AM, Chan, WCW, Bhatia, SN. Probing cytotoxcity of semiconductor quantum dots. Nato Letters 4, 11-18, 2004.
Dewerchin M, Nuffelen AV, Wallays G, Bouche A, Moons L, Carmeliet P, Mulligan RC, Collen D. Generation and characterization of urokinase receptor-deficient mice. J Clin Invest 1996;97:870-8.
Ellerby HM, Arap W, Ellerby LM, Kain R, Andrusiak R, Rio GD, Krajewski S, Lombardo CR, Rao R, Ruoslahti E, Bredesen DE, Pasqualini R. Anti-cancer activity of targeted pro-apoptotic peptides. Nat Med 1999;5;9:1032-8.
Frank JA, Miller BR, Arbab AS, Zywicke HA, Jordan EK, Lewis BK, Bryant LH, Jr., Bulte JW. Clinically applicable labeling of mammalian and stem cells by combining superparamagnetic iron oxides and transfection agents. Radiology 2003;228;2:480-7.
Funovics MA, Kapeller B, Hoeller C, Su HS, Kunstfeld R, Puig S, Macfelda K. MR imaging of the her2/neu and 9.2.27 tumor antigens using immunospecific contrast agents. Magn Reson Imaging 2004;22:843-50.
Gao X, Cui Y, Levenson RM, Chung LW, Nie S. In vivo cancer targeting and imaging with semiconductor quantum dots. Nat Biotechnol 2004;22:8:969-76.
Gao X, Nie S. Quantum dot-encoded mesoporous beads with high brightness and uniformity: rapid readout using flow cytometry. Anal Chem 2004;76:8:2406-10.
Guo W, Li JJ, Wang YA, Peng X. Luminescent CdSe/CdS core/shell nanocrystals in dendron boxes: superior chemical, photochemical and thermal stability. J Am Chem Soc 2003;125:13:3901-9.
Gupta AK, Gupta M. Synthesis and surface engineering of iron oxide nanoparticles for biomedical applications. Biomaterials 2005;26:3995-4021.
Hainfeld JF, Liu W, Halsey CM, Freimuth P, Powell RD. Ni-NTA-gold clusters target His-tagged proteins. J Struct Biol 1999;127:185-98.
Hallahan D, Geng L, Qu S, Scarfone C, Giorgio T, Donnelly E, Gao X, Clanton J. Integrin-mediated targeting of drug delivery to irradiated tumor blood vessels. Cancer Cell. Jan. 2003;3:63-74.
Hanahan D, Weinberg RA. The hallmarks of cancer. Cell Jan. 7, 2000;100:57-70.
Harisinghani MG, Barentsz J, Hahn PF, Deserno WM, Tabatabaei S, van de Kaa CH, de la Rosette J, Weissleder R. Noninvasive detection of clinically occult lymph-node metastases in prostate cancer. N Engl J Med Jun. 19, 2003;348;25;2491-9.
Harris RC, Chung E, Coffey RJ. EGF receptor ligands. Exp Cell Res 2003;284:2-13.
Hemsen A, Riethdorf L, Brunner N, Berger J, Ebel S, Thomssen C, Janicke F, Pantel K. Comparative evaluation of urokinase-type plasminogen activator receptor expression in primary breast carcinomas and on metastatic tumor cells. Int J Cancer 2003;107:903-9.
Hood JD, Bednarski M, Frausto R, Guccione S, Reisfeld RA, Xiang R, Cheresh DA. Tumor regression by targeted gene delivery to the neovasculature. Science Jun. 28, 2002;296:2404-7.
Ignar DM, Andrews JL, Witherspoon SM, Leray JD, Clay WC, Kilpatrick K, Onori J, Kost T, Emerson DL. Inhibition of establishment of primary and micrometastatic tumors by a urokinase plasminogen activator receptor antagonist. Clin Exp Metastasis 1998;16(1):9-20.
Jain RK. Delivery of molecular and cellular medicine to solid tumors. Adv Drug Deliv Rev 1997;26:71-90.
Jain RK. Transport of molecules, particles, and cells in solid tumors. Annu Rev Biomed Eng 1999;1:241-63.
Kim E.S, Khuri F.R., Herbst RS. Epidermal growth factor receptor biology (IMC-C225). Curr Opin Oncol 2001;13:506-13.
Kim S, Lim YT, Soltesz EG, De Grand AM, Lee J, Nakayama A, Parker JA, Mihaljevic T, Laurence RG, Dor DM, Cohn LH, Bawendi MG, Frangioni JV. Near-infrared fluorescent type II quantum dots for sentinel lymph node mapping. Nat Biotechnol 2004;22(1):93-7.
Kizaka-Kondoh S, Inoue M, Harada H, Hiraoka M. Tumor hypoxia: A target for selective cancer therapy. Cancer Sci Dec. 2003;94(12):1021-8.
Kobayashi H, and Brechbiel MW. Dendrimer-based nanosized MRI contrast agents. Curr Pharm Biotechnol 2004;5:539-49.
Law B, Curino A, Bugge TH, Weissleder R, Tung CH. Design, synthesis, and characterization of urokinase plasminogen-activator-sensitive near-infrared reporter. Chem Biol Jan. 2004;11:99-106.
Li H, Lu H, Griscelli F, Opolon P, Sun LQ, Ragot T, Legrand Y, Belin D, Soria J, Soria C, Perricaudet M, Yeh P. Adenovirus-mediated delivery of a uPA/uPAR antagonist suppresses angiogenesis-dependent tumor growth and dissemination in mice. Gene Ther 1998;5:1105-13.
Liu D, Aguirre Ghiso J, Estrada Y, Ossowski L. EGFR is a transducer of the urokinase receptor initiated signal that is required for in vivo growth of a human carcinoma. Cancer Cell Jun. 2002;1:445-57.
Mahmood U. and Weissleder R. Near-infrared optical imaging of proteases in cancer. Mol Cancer Ther. May 2003;2:489-96.
Mai JC, Mi Z, Kim SH, Ng B, Robbins PD. A proapoptotic peptide for the treatment of solid tumors. Cancer Res Nov. 1, 2001;61:7709-12.
Meijer-van Gelder ME, Look MP, Peters HA, Schmitt M, Brunner N, Harbeck N, Klijn JG, and Foekens JA. Urokinase-type plasminogen activator system in breast cancer: association with tamoxifen therapy in recurrent disease. Cancer Res. Jul. 1, 2004;64:4563-8.
Mendelsohn J. Targeting the epidermal growth factor receptor for cancer therapy. J. Clin. Oncol. 2002;20(18s):1S-13S.
Moon WK, Lin Y, O'Loughlin T, Tang Y, Kim DE, Weissleder R, Tung CH. Enhanced tumor detection using a folate receptor-targeted near-infrared fluorochrome conjugate. Bioconjug Chem 2003;14:539-45.
Newkome GR, Childs BJ, Rourk MJ, Baker GR, and Moorefield CN. Dendrimer construction and macromolecular property modification via combinatorial methods. Biotechnol Bioeng 1998/1999;61(4):243-53.
Nicholson RI, Gee JM, and Harper ME. EGFR and cancer prognosis. Eur J Cancer. Mar. 7, 2001;37 Suppl 4:S9-15.
Oca-Cossio J, Mao H, Khokhlova N, Kennedy CM, Kennedy JW, Stabler CL, Hao E, Sambanis A, Simpson NE, and Constantinidis I. Magnetically labeled insulin-secreting cells. Biochem Biophys Res Commun 2004;319:569-75.
Padera TP, Stoll BR, Tooredman JB, Capen D, di Tomaso E, and Jain RK. Pathology: cancer cells compress intratumour vessels. Nature Feb. 19, 2004;427:695.
Rabbani SA, Mazar AP. The role of the plasminogen activation system in angiogenesis and metastasis. Surg Oncol Clin N Am 2001;10:393-415, x.
Rajagopal V. and Kreitman RJ. Recombinant toxins that bind to the urokinase receptor are cytotoxic without requiring binding to the alpha(2)-macroglobulin receptor. J Biol. Chem. Mar. 17, 2000;275(11):7566-73.
Romer J, Nielsen BS, and Ploug M. The urokinase receptor as a potential target in cancer therapy. Curr Pharm Des 2004;10:2359-76.
Ruscowski M, Qu T, Chang F, Hnatowich DJ. Technetium-99m labeled epidermal growth factor-tumor imaging in mice. J Pept Res 1997;50:393-401.
Schirner M, Menrad A, Stephens A, Frenzel T, Hauff P, Licha K. Molecular imaging of tumor angiogenesis. Ann N Y Acad Sci 2004;1014:67-75.

Schmitt J, Hess H, Stunnenberg HG. Affinity purification of histidine-tagged proteins. Mol Biol Rep 1993;18:223-30.

Shinkai M, Ito A. Functional magnetic particles for medical application. Adv Biochem Eng Biotechnol 2004;91:191-220.

Solbach C, Roller M, Ahr A, Loibl S, Nicoletti M, Stegmueller M, Kreysch HG, Knecht R, Kaufmann M. Anti-epidermal growth factor receptor-antibody therapy for treatment of breast cancer. Int J Cancer 2002;101:390-4.

Solberg H, Ploug M, Hoyer-Hansen G, Nielsen BS, Lund LR. The murine receptor for urokinase-type plasminogen activator is primarily expressed in tissues actively undergoing remodeling. J Histochem Cytochem 2001;49(2):237-46.

Soling A, Rainov NG. Bioluminescence imaging in vivo—application to cancer research. Expert Opin Biol Ther 2003;3:1163-72.

Soltesz EG, Kim S, Laurence RG, DeGrand AM, Parungo CP, Dor DM, Cohn LH, Bawendi MG, Frangioni JV, Mihaljevic T. Intraoperative sentinel lymph node mapping of the lung using near-infrared fluorescent quantum dots. Ann Thorac Surg 2005;79:269-77; discussion 269-77.

Sorkin A. Internalization of the epidermal growth factor receptor: role in signalling. Biochem Soc Trans 2001;29 (pt.4):480-4.

Sun et al., Monodisperse FePt Nanoparticles and Ferromagnetic FePt Nanocrystal Superlattices, Science, Mar. 17, 2000;287;1989-1992.

Sundstrom JB, Mao H, Santoianni R, Villinger F, Little DM, Huynh TT, Mayne AE, Hao E, Ansari AA. Magnetic resonance imaging of activated proliferating rhesus macaque T cells labeled with superparamagnetic monocrystalline iron oxide nanoparticles. J Acquir Immune Defic Syndr., Jan. 1, 2004;35(1):9-21.

Tsutsui S, Ohno S, Murakami S, Hachitanda Y, Oda S. Prognostic value of epidermal growth factor receptor (EGFR) and its relationship to the estrogen receptor status in 1029 patients with breast cancer. Breast Cancer Res Treat 2002;71:67-75.

Vilhardt F, Nielsen M, Sandvig K, van Deurs B. Urokinase-type plasminogen activator receptor is internalized by different mechanisms in polarized and nonpolarized Madin-Darby canine kidney epithelial cells. Mol Biol Cell Jan. 1999;10:179-95.

Wang Ya, Li JJ, Chen H, Peng X. Stabilization of inorganic nanocrystals by organic dendrons. J Am Chem Soc 2002;124(10):2293-8.

Wikstrand CJ, McLendon RE, Friedman AH, Bigner DD. Cell surface localization and density of the tumor-associated variant of the epidermal growth factor receptor, EGFRvIII. Cancer Res. Sep. 15, 1997;57:4130-40.

Wood, J., Nanoparticles Seek Out and Destroy Cancer, Materials Today, Sep. 2004;12.

Ugrinska, A., Bombardieri, E., Stokkel, PM., Crippa, F., and Pauwels, EK. Circulating tumor markers and nuclear medicine imaging modalities: breast, prostate and ovarian cancer. QJ Nucl Med. Jun. 2002;46;88-104.

Zhao M., Kircher MF, Josephson L., and Weissleder R., Differential conjugation of tat peptide to superparamagnetic nanoparticles and its effect on cellular uptake. Bioconj. Chem. 2002;13;840-844.

\* cited by examiner

A. Conditional delivery of an apoptosis inducing peptide (KLAKLAK)2:

SEQ ID NO: 1  NH3-His-His-His-His-His-His-PLGLWAR*GRKKRRQRRR*(KLAKLAKLAKLAK)-COOH

| 6x His tag | MMP cleavage site | Tat delivery into cells | Apoptosis inducer |

MMP activity is high in breast cancer

B. Apoptosis-inducing peptide induces cell death in mouse and human breast cancer

US 8,394,760 B2

MULTIFUNCTIONAL NANOSTRUCTURES, METHODS OF SYNTHESIZING THEREOF, AND METHODS OF USE THEREOF

CROSS-REFERENCE TO RELATED PATENT APPLICATION

This application claims the benefit, pursuant to 35 U.S.C. §119(e), of U.S. provisional patent application Ser. No. 60/676,812, filed May 2, 2005, entitled "TARGETED MULTIFUNCTIONAL NANOPARTICLES FOR IN VIVO IMAGING AND TREATMENT," by Lily Yang, Shuming Nie, Xiaohu Gao and Xiang Hong Peng, which is incorporated herein by reference in its entirety.

STATEMENT AS TO RIGHTS UNDER FEDERALLY-SPONSORED RESEARCH

This invention was made with Government support under Contract Nos. R01CA095643, R01GM058173 and R01CA108468 awarded by the National Institutes of Health of the United States, and under Contract No. DAMD17-03-1-0665 awarded by the Department of Defense of the United States. The government has certain rights in the invention.

This application is being filed as PCT International Patent application in the name of Emory University, a U.S. national corporation, Applicants for all countries except the U.S., and Lily Yang, Shuming Nie, Xiaohu Gao and Xiang Hong Peng, all U.S. residents, Applicants for the designation of the U.S. only, on 2 May 2006.

This application is related to a copending U.S. patent application entitled "Bioconjugated nanostructures, methods of fabrication thereof, and methods of use thereof", U.S. patent application Ser. No. 10/988,923, filed 15 Nov. 2004 with the same assignee as the present invention. The two applicants of the above identified copending applications are also applicants of this application. The disclosure of the above identified copending applications is incorporated herein by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [48] represents the 48th reference cited in the reference list, namely, Gao X, Nie S. Quantum dot-encoded mesoporous beads with high brightness and uniformity: rapid readout using flow cytometry. Anal Chem 2004; 76:2406-10.

FIELD OF THE INVENTION

The present invention relates generally to nanostructures, and in particular to multifunctional nanostructures for in vivo tumor imaging and treatment.

BACKGROUND OF THE INVENTION

The application of nanotechnology to cancer research is an exciting frontier in the efforts to develop novel approaches for cancer detection and treatment. Although the feasibility of using nanoparticles for cancer detection and drug delivery has been demonstrated in several laboratories [1-3], a major obstacle limiting its clinical application is that non-tumor targeted nanoparticles are unable to reach sufficient concentration in the tumor site to either produce a strong signal for tumor imaging or to carry optimal amounts of therapeutic agents into tumor cells.

Breast cancer is the most common type of cancer and a leading cause of death among women. Crucial factors that would increase patient survival are early detection and effective treatment. The development of novel approaches for detecting and treating breast cancer are urgently needed to increase patient survival. Furthermore, since cancer metastasis is the main cause for the mortality in breast cancer patients. Any new approaches for detection and targeted treatment of distant metastases should also significantly improve patient prognosis.

Although various imaging technologies and modalities have been widely used for management of cancer including diagnosis and treatment monitoring, conventional tumor imaging methods such as MRI, CT or even PET have their limitations in both specificity and sensitivity of cancer detection [4-6]. Increasing evidence suggests that use of targeted imaging probes enhances signal intensity in the tumor, increasing the sensitivity of the detection [7-10]. Furthermore, imaging agents that target changes in the tumor environment, such as tumor endothelial cells and intra-tumor stromal cells, should further augment tumor imaging signals [11].

It is clear that selective delivery of therapeutic agents into a tumor mass has the potential to minimize toxicity to normal tissues, while improving bioavailability of cytotoxic agents in the tumor [12, 13]. Antibodies, ligands and peptides that target to cell surface molecules, which are highly expressed in tumor cells or tumor endothelial cells have been used to deliver therapeutic agents, showing promise in achieving tumor specific cytotoxicity [3, 14]. An important way to improve the delivery of therapeutic agents is to limit the size of the delivery complex in many currently used delivery systems such as antibody-conjugates, liposomes and other macromolecules, since it is well known that solid tumors will show very poor bio-distribution of the large molecules due to the dysfunctional blood and lymphatic vessels and compressive pressure in the tumor [15-17]. Therefore, the use of drug delivery vehicles with sizes of a few nanometers will enhance the efficiency of delivery of therapeutic agents into solid tumors.

Additionally, tumor imaging plays a key role in helping clinicians to detect solid tumors, to determine tumor recurrence and to evaluate the response of the tumors to therapeutic reagents. The combination of imaging technology and tumor biology have created a "molecular imaging" field with new applications in all imaging modalities. The methods for high-resolution in vivo imaging using mainly three types of imaging probes: radio-labeled, magnetic and optical probes for positron emission tomography (PET) and single photon emission tomography (SPECT); MRI and spectroscopy; and optical imaging techniques, including fluorescence-mediated tomography (FMT) and near-infrared fluorescence (NIRF) reflectance imaging. Although different modalities vary in imaging sensitivity and resolution, the technical challenge in improving target specificity and sensitivity is common. In a clinical practice, for example, $^{18}$F-fluoro-2-deoxy-D-glucose (FDG) and Gd(III)-aminobenzyl-diethylenetriaminepentaacetic acid (Gd-DTPA) contrast agent are used commonly for PET and MRI respectively. However, both have significant limitations in sensitivity and specificity in delineating tumor and detecting cancer cells in the early stage of development of tumor [5. 44, 45]. Recently, tumor-targeted optical, radio- or magnetic probes have been generated and the feasibility of those imaging probes was examined in both animal tumor models and in clinical studies [1, 7, 10, 46, 47]. Those results show that tumor-targeted imaging probes can increase the localization of the image probes in tumors while reducing their uptake in normal tissues. However, to develop a promising tumor imaging approach to clinical applications, several important issues have to be addressed in the research laboratory. The most important issues include: 1) developing of imaging probes that emit a strong signal to improve sensitivity of detection; 2) targeting probes to cellular receptors that are highly expressed in human tumor cells or tumor environments and demonstrating that there is low toxicity to normal organs and tissues; and 3) developing an effective delivery system to direct the imaging probe to the targeted tumor or cancer cells.

At present, three types of imaging probes are used for in vivo imaging: optical, magnetic and radio labeled probes. Optical image probes use organic fluorescence dyes, fluorescence proteins, and semiconductor quantum dots. Emerging as a new class of fluorescent probes for in vivo biomolecular and cellular imaging, these quantum dots (QDs) are tiny, nanometer-scale light-emitting particles. In comparison with organic dyes and fluorescent proteins, quantum dots have unique optical and electronic properties such as size-tunable light emission, improved signal brightness, resistance against photobleaching, and ability to simultaneous excite multiple fluorescence colors [48]. These properties are most promising for improving the sensitivity of molecular imaging and quantitative cellular analysis by 1-2 orders of magnitude. Nie et al. first reported that it is feasible to simultaneously target and image prostate tumors in living animal models using bioconjugated prostate membrane antigen-targeted QDs [1]. This new class of QD conjugates contains an amphiphilic triblock copolymer layer for in vivo protection and multiple PEG molecules for improved biocompatibility and circulation, making it highly stable and able to produce bright signals. This triblock copolymer layer is designed so that it can have multiple active functional groups for conjugation of different tumor targeting moieties and therapeutic agents on the same nanoparticle. Another advantage is that multicolor QD probes can be used to image and track multiple tumor markers simultaneous, which will most likely increase the specificity and sensitivity of cancer detection.

Recently, QDs producing near infrared (NIR) signals have also been developed [49, 50]. NIR light penetrates much more deeply into tissues, compared to visible fluorescence, and allows detection of signals inside animals. The feasibility of detection of NIR signals in animal tumor models has been demonstrated using fluorescent dye Cy 5.5-labeled RGD peptide or an enzyme-activated Cy 5.5 NIR signal [10, 51, 52]. Detection of QD NIR signals in sentinel lymph node in large animals real time has also been demonstrated [50, 53]. A major advantage of NIR QDs is that emissions of those QDs are well beyond the spectral range of autofluorescence in tissues, thus resulting in imaging with a high signal: background ratio [53].

In comparison to optical imaging, magnetic resonance imaging (MRI) has lower sensitivity when applied for molecular and cellular imaging. However, it has super imaging resolution and deep tissue penetration for visualizing abnormalities in small animal and human using tissue water molecules as signal sources. It is a non-invasive imaging modality and routinely used in the clinic for diagnostic imaging. To obtain contrast enhancement and signal amplification, paramagnetic contrast agents are often used. Although Gd-DTPA, a blood-pool contrast agent, is widely accepted in the clinical uses, superparamagentic IO nanoparticle is emerging as a new generation of MRI contrast agent for the development of target specific contrast agent, because it has a long blood retention time, low toxicity and biodegradability. The IO nanoparticles possess unique paramagnetic properties, which generate significant susceptibility changes resulting in strong $T_2$ and $T^*_2$ contrast [45, 54]. In addition, the surface coating molecules used for IO nanoparticles can be conjugated to the biomolecule to provide target specific interaction to the cell [54]. Several recent studies have demonstrated that IO nanoparticles can be internalized by various cell lines including cancer cells to allow magnetically labeling of the targeted cell. When internalized by cells, IO nanoparticles are able to generate MRI contrast that enables single-cell MR detection [55]. At present, non-targeted IO particles has been used in clinic and is proven to be safe for human use.

Over the past years, significant efforts have gone toward developing a target specific MRI contrast agent based on the formulation of the IO nanoparticle [56-59]. However, several obstacles remain to be overcome. The major challenge is to develop a surface coating material that not only can stabilize the nanoparticle but also to provide active functional groups available for controllable bioconjugation of "probe" ligands. Traditional ligands (e.g., dextran) that are used for the stabilization of magnetic nanocrystals often have weak ligand-particle interactions, so they can be easily detached from the nanocrystal surface, leading to nanoparticle aggregation and eventually precipitation even under physiological conditions or even just during storage. Since further derivatization is needed, such a weak interaction between ligand and particle may not withstand the required reaction conditions.

Therefore, a heretofore-unaddressed need exists in the art to address the aforementioned deficiencies and inadequacies.

SUMMARY OF THE INVENTION

The present invention, in one aspect, relates to a nanostructure. In one embodiment, the nanostructure comprises a nanospecies, a hydrophobic protection structure including at least one compound selected from a capping ligand, an amphiphilic copolymer, and combinations thereof, wherein the hydrophobic protection structure encapsulates the nanospecies, and at least one histidine-tagged peptide or protein conjugated to the hydrophobic protection structure, wherein the at least one histidine-tagged peptide or protein has at least one binding site.

The amphiphilic copolymer is selected from amphiphilic block copolymers, amphiphilic random copolymers, amphiphilic alternating copolymers, amphiphilic periodic copolymers, and combinations thereof. In one embodiment, the amphiphilic copolymer is a block copolymer selected from a diblock copolymer, a triblock copolymer, and combinations thereof. The amphiphilic block copolymer includes an ABC triblock structure having grafted 8-carbon alkyl side chains, wherein the ABC triblock structure includes a poly-butylacrylate segment, a poly-ethylacrylate segment, and a poly-methacrylic acid segment. In one embodiment, the amphiphilic copolymer has a molecular weight of about 50,000 Da to 200,000 Da, preferably about 100,000 Da.

The nanospecies is selected from a quantum dot, a metallic nanoparticle, and a metal oxide nanoparticle. The quantum dot comprises a core and a cap. In one embodiment, the core of the quantum dot is selected from the group consisting of IIA-VIA semiconductors, IIIA-VA semiconductors, IVA- IVA semiconductors, and IVA-VIA semiconductors. In another embodiment, the core of the quantum dot is selected from the group consisting of IIA-VIA semiconductors. In an alternative embodiment, the core of the quantum dot is CdSe. In one embodiment, the quantum dot is CdTe/CdSe.

The cap is selected from the group consisting of IIA-VIA semiconductors of high band gap. In one embodiment, the cap comprises ZnS.

The nanostructure may further comprise a bio-compatibility compound substantially disposed on the hydrophobic protection structure, wherein the bio-compatibility compound is a polyethylene glycol molecule having a molecular weight of about 500 Da to 50,000 Da.

The nanostructure may also comprise a probe disposed on the hydrophobic protection structure or on the binding site of the at least one histidine-tagged peptide or protein, wherein the probe is selected from an antibody, a polypeptide, a polynucleotide, a drug molecule, an inhibitor compound, and combinations thereof. In one embodiment, the probe comprises a drug, a therapeutic agent, a radiological agent, a molecule drug, and any combinations thereof.

Additionally, the nanostructure includes a chelating compound conjugating the at least one histidine-tagged peptide or protein to the hydrophobic protection structure by forming two or more coordinating bonding with the at least one histidine-tagged peptide or protein and the hydrophobic protection structure, respectively, wherein the chelating compound comprises nickel-nitrilotriacetic acid (Ni-NTA).

The capping ligand includes tri-octylphosphine oxide.

The at least one histidine-tagged peptide or protein in one embodiment comprises a histidine-tagged amino-terminal fragment (ATF) of urokinase plasminogen activator (uPA). In another embodiment, the at least one histidine-tagged peptide or protein comprises a histidine-tagged epidermal growth factor receptor (EGFR) single chain antibody (ScFv EGFR).

The binding site of the at least one histidine-tagged peptide or protein can be at the C-terminal, N-terminal or inside of the peptide or protein between two functional domains on the peptide or protein.

In another aspect, the present invention relates to a method of synthesizing a nanostructure. In one embodiment, the method includes the steps of providing a nanospeices, forming a hydrophobic protection structure around the nanospeices that includes at least one compound selected from a capping ligand, an amphiphilic copolymer, and combinations thereof, and conjugating at least one histidine-tagged peptide or protein to the hydrophobic protection structure, wherein the at least one histidine-tagged peptide or protein has at least one binding site.

The method may further comprise the step of attaching a bio-compatibility compound to the hydrophobic protection structure.

The method may also comprise the step of attaching a probe to the hydrophobic protection structure or the at least one binding site of the at least one histidine-tagged peptide or protein.

The probe is selected from an antibody, a polypeptide, a polynucleotide, a drug molecule, an inhibitor compound, and combinations thereof. In one embodiment, the probe comprises a drug, a therapeutic agent, a radiological agent, a molecule drug, and any combinations thereof.

The nanospecies is a quantum dot and the hydrophobic protection structure including the capping ligand and the amphiphilic copolymer. The amphiphilic copolymer comprises a block copolymer that is selected from a diblock copolymer, a triblock copolymer, and combinations thereof.

The capping ligand includes tri-octylphosphine oxide, and wherein the amphiphilic copolymer is an ABC triblock structure that includes a poly-butylacrylate segment, a poly-ethylacrylate segment, and a poly-methacrylic acid segment.

The conjugating step is performed with a chelating compound. The chelating compound comprises nickel-nitrilotriacetic acid (Ni-NTA).

In yet another aspect, the present invention relates to a nanostructure. In one embodiment, the nanostructure includes a nanospeices, at least one histidine-tagged peptide or protein conjugated to the nanospeices, wherein the at least one histidine-tagged peptide or protein has at least one binding site, and a probe coupled to the nanospeices or to the at least one binding site of the at least one histidine-tagged peptide or protein. In one embodiment, the nanospecies is selected from a quantum dot, a metallic nanoparticle, and a metal oxide nanoparticle.

The nanostructure may comprise a hydrophobic protection structure including at least one compound selected from a capping ligand, an amphiphilic copolymer, and combinations thereof, wherein the hydrophobic protection structure encapsulates the nanospecies.

The nanostructure further includes a chelating compound for conjugating at least one histidine-tagged peptide or protein to the nanospeices, wherein the chelating compound comprises nickel-nitrilotriacetic acid (Ni-NTA).

In one embodiment, the at least one histidine-tagged peptide or protein comprises a histidine-tagged amino-terminal fragment (ATF) of urokinase plasminogen activator (uPA). In another embodiment, the at least one histidine-tagged peptide or protein comprises a histidine-tagged epidermal growth factor receptor (EGFR) single chain antibody (ScFv EGFR).

In one embodiment, the binding site of the at least one histidine-tagged peptide or protein can be at the C-terminal, N-terminal or inside of the peptide or protein between two functional domains on the peptide or protein.

The probe is selected from an antibody, a polypeptide, a polynucleotide, a drug molecule, an inhibitor compound, and combinations thereof. In one embodiment, the probe is a probe molecule that has an affinity for one or more target molecules. In another embodiment, the probe is a drug, a therapeutic agent, a radiological agent, a molecule drug, and any combinations thereof.

In a further aspect, the present invention relates to a method of detecting a target in a subject. In one embodiment, the method includes the steps of providing a nanostructure having: at least one nanospecies, a hydrophobic protection structure including at least one compound selected from a capping ligand, an amphiphilic copolymer, and combinations thereof, wherein the hydrophobic protection structure encapsulates the nanospecies, at least one histidine-tagged peptide or protein conjugated to the nanospeices, wherein the at least one histidine-tagged peptide or protein has at least one binding site, and at least one probe coupled to the nanospeices or to the at least one binding site of the at least one histidine-tagged peptide or protein, wherein a first probe has an affinity of the target. The method further includes the steps of introducing the nanostructure to a subject, and determining the presence of the target in the subject corresponding to the first probe by detecting the nanospecies. The determination is made in-vivo.

The target can be a cancerous disease, a tumor, or a cancer such as a breast cancer.

The probe is selected from an antibody, a polypeptide, a polynucleotide, a drug molecule, an inhibitor compound, and combinations thereof. In one embodiment, the probe comprises a drug, a therapeutic agent, a radiological agent, a molecule drug, and any combinations thereof.

The nanostructure includes a second probe that can be a drug molecule, and wherein the drug molecule is effective at treating the disease.

The introduction can be performed by a subcutaneous injection or a systemic injection. The determination includes a targeting process selected from a passive targeting process and an active targeting process.

In yet a further aspect, the present invention relates to a nanostructure. In one embodiment, the nanostructure comprises a superparamagnetic iron oxide (IO) nanocrystal, a protection structure including at least an asymmetric dendrimer, wherein the protection structure encapsulates the superparamagnetic IO nanocrystal, and at least one histidine-tagged peptide or protein conjugated to the protection structure, wherein the at least one histidine-tagged peptide or protein has at least one binding site.

The nanostructure further comprises a chelating compound conjugating the at least one histidine-tagged peptide or protein to the protection structure, wherein the chelating compound comprises nickel-nitrilotriacetic acid (Ni-NTA).

The nanostructure may also comprise a probe coupled to the protection structure or to the at least one binding site of the at least one histidine-tagged peptide or protein.

The asymmetric dendrimer is adapted for substituting small molecules of citrate on the surface of the superparamagnetic iron oxide particle, which retains the superparamagnetic properties of the IO nanocrystal, but with the surface functionalized for conjugating the at least one histidine-tagged peptide or protein.

In one embodiment, the IO nanocrystal has a size of about 5 nm. The 10 nanocrystal is detectable by magnetic resonance imaging (MRI)

The binding site of the at least one histidine-tagged peptide or protein can be at the C-terminal, N-terminal or inside of the peptide or protein between two functional domains on the peptide or protein.

The tumor targeting agent comprises a tumor targeting peptide, protein ligand, antibody, inhibitor, small molecular drug, or any combination thereof, wherein in use, the tumor targeting agent selectively bonds to one or more tumor cells of a subject for identification and/or therapeutic treatment of the tumor cells.

In yet another aspect, the present invention relates to a method for synthesizing a nanostructure. In one embodiment, the method includes the steps of providing a superparamagnetic iron oxide (IO) nanocrystal and at least one histidine-tagged peptide or protein, and conjugating at least one histidine-tagged peptide or protein to the IO nanocrystal.

The method further comprises the step of coating the superparamagnetic 10 nanocrystal with an asymmetric dendrimer.

In one embodiment, the conjugating step comprises the step of linking the at least one histidine-tagged peptide or protein to the coated superparamagnetic 10 nanocrystal by nickel-nitrilotriacetic acid (Ni-NTA).

In one embodiment, the at least one histidine-tagged peptide or protein comprises a histidine-tagged amino-terminal fragment (ATF) of urokinase plasminogen activator (uPA). In another embodiment, the at least one histidine-tagged peptide or protein comprises a histidine-tagged epidermal growth factor receptor (EGFR) single chain antibody (ScFv EGFR).

In a further aspect, the present invention relates to a method for target imaging and/or therapy. In one embodiment, the method comprises the steps of providing a nanostructure having: a superparamagnetic iron oxide (IO) nanocrystal, a protection structure including at least an asymmetric dendrimer, wherein the protection structure encapsulates the superparamagnetic IO nanocrystal, at least one histidine-tagged peptide or protein conjugated to the protection structure, wherein the at least one histidine-tagged peptide or protein has at least one binding site, and a probe coupled to the protection structure or the at least one binding site of the at least one histidine-tagged peptide or protein, introducing the nanostructure into a subject, and determining the presence of the target in the subject corresponding to the targeting agent by detecting the nanospecies.

In one embodiment, the target can be a cancerous disease, a tumor, or a cancer such as a breast cancer.

The determination is made by acquiring an image of the target, and includes a targeting process selected from a passive targeting process and an active targeting process.

The introduction is performed by a subcutaneous injection or a systemic injection.

The subject can be a living subject such as an animal or a human being.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE PREFERRED EMBODIMENTS

Figure 1:
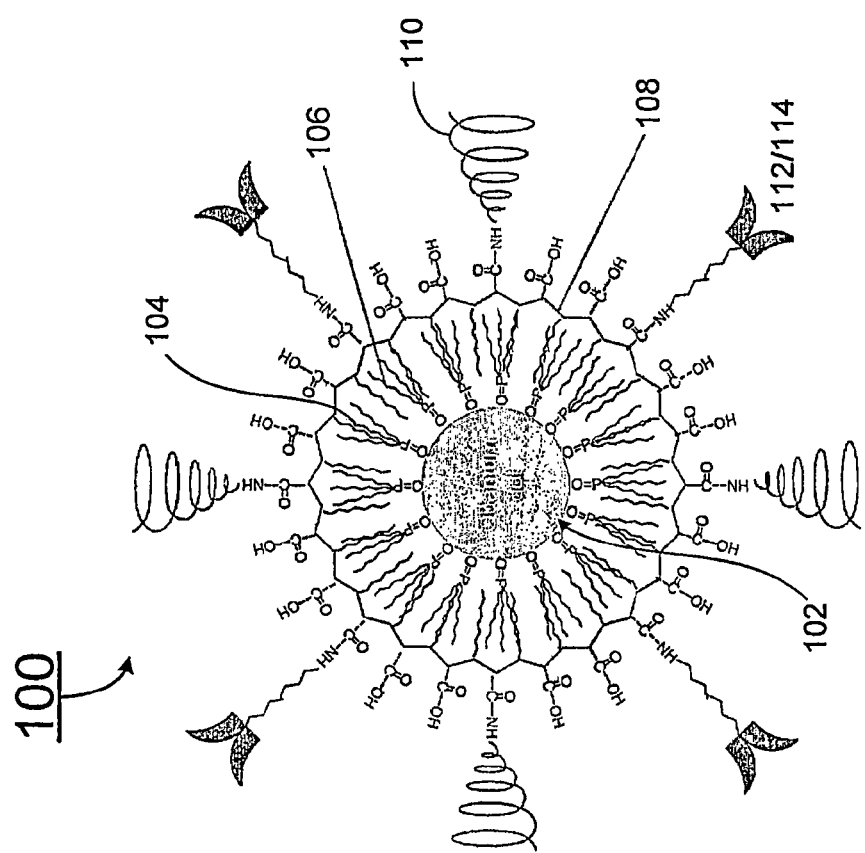
FIG. 1 shows schematically a multifunctional nanostructure according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "quantum dot" as used herein refers to a quantum-confined particle or a semiconductor crystal that confines electrons, holes, or electron-hole pairs or so-called excitons to a region on the order of just a few nanometers. The quantum dot (QD) exhibits unique optical and electronic properties, such as size- and composition-tunable fluorescence emission from visible to infrared wavelengths, large absorption coefficients across a wide spectral range, and very high levels of brightness and photostability.

The term "histidine-tag" as used herein refers to an amino acid motif in proteins that consists of at least six histidine (His) residues, often at the N- or C-terminus of the protein.

The term "copolymer" as used herein refers to a polymer formed when two (or more) different types of monomer are linked in the same polymer chain. The assembly of the monomers in the copolymers can be head-to-tail, head-to-head, or tail-to-tail. Since a copolymer consists of at least two types of repeating units (not structural units), copolymers can be classified, based on how these units are arranged along the chain, as random copolymer, alternating copolymer, block copolymer, graft copolymer, star copolymers, and brush copolymers The block copolymers are made up of blocks of different polymerized monomers. For example, polystyrene-b-poly (methyl methacrylate) (PS-b-PMMA) is made by first polymerizing styrene, and then subsequently polymerizing MMA. This polymer is a diblock copolymer because it contains two different chemical blocks. One can also make triblocks, tetrablocks, pentablocks, etc.

The term "dendrimer" as used herein refers to a molecule with a form like the branches of a tree. The properties of dendrimers are dominated by the functional groups on the molecular surface. For example, a dendrimer can be water-soluble when its end-group is a hydrophilic group, like a carboxyl group. For a water-soluble dendrimer with internal hydrophobicity, it can be used to carry a hydrophobic drug in its interior. Another property of dendrimers is that the volume of a dendrimer increases when it has a positive charge. If this property can be applied, dendrimers can be used for drug delivery systems (DDS) that can give medication to the affected part inside a patient's body directly.

Acronyms and abbreviations used herein, "Ni-NTA" refers to nickel-nitrilotriacetic acid; "ATF" refers to an amino-terminal fragment; "uPA" refers to a urokinase plasminogen activator; "EGFR" stands for an epidermal growth factor receptor; "ScFv EGFR" represents an EGFR single chain antibody; "QD" stands for a quantum dot; "10" represents an iron oxide; "ATF-QDs" refers to histidine-tagged ATF conjugated quantum dots; "ScFv EGFR-QDs" refers to histidine-tagged ScFv EGFR conjugated quantum dots; ATF-IO" refers to a histidine-tagged ATF conjugated iron oxide; and "ScFv EGFR-QDs" refers to a histidine-tagged ScFv EGFR conjugated iron oxide.

Overview of the Invention

Development of human cancer is a multistage process involving various genetic alternations and cellular abnormalities that provide advantages for the growth and progression of tumors [18]. The differences in the expression of cellular receptors between normal and tumor cells provide a great opportunity for targeting nanoparticles to the altered cancer cell surface molecules.

Urokinase plasminogen activator (uPA) is a serine protease that regulates multiple pathways involved in matrix degradation, cell motility, metastasis and angiogenesis [6, 19]. Interaction of the N-terminal growth factor domain of uPA with its cellular receptor (uPAR) results in the conversion of the plasminogen to a serine protease, which is a central regulator of the activation of other proteases including the matrix metalloproteinases (MMPs) [19]. Studies have shown that the uPA/uPAR complex controls the motility of both tumor and endothelial cells [20]. In addition to its role in activation of the process for degradation of extracellular matrix, uPAR also activates α5β1 integrin and ERK signaling through interaction with EGFR and induces cell proliferation [21]. Additionally, the uPA/uPAR complex can bind to the matrix protein, vitronectin, in association with transmembrane integrins, and activate intracellular signaling molecules such as the protein kinases, promoting cell adhesion, proliferation, and migration [22].

The cellular receptors for uPA (uPAR) are highly expressed in many human tumor cells, intratumoral fibroblasts and tumor endothelial cells. About 54% of ductal carcinoma in situ (DCIS) and 73% of lobular carcinoma tissues have over 50% of their cancer cells overexpressing uPAR [23]. An elevated level of uPAR is associated with tumor aggressiveness, the presence of distant metastasis and poor prognosis [24]. However, uPAR is undetectable in the majority of normal tissues or organs except for low levels expressed in macrophages, granulocytes, the uterus, thymus, kidney and spleen [25]. Therefore, uPAR is an excellent molecular target for recruiting nanoparticles to breast tumor sites.

The uPAR-binding domain of uPA is located to the amino-terminal fragment (ATF) of uPA [26]. Studies have shown that ATF is a potent uPA binding antagonist to its high affinity receptor (uPAR) at the surface of both tumor and endothelial cells [27, 28]. Systemic or local delivery of a non-catalytic amino-terminal fragment (ATF) of uPA (residues 1-135) using an adenoviral vector or conjugated peptides prevents the formation of the uPA/uPAR complex, thus inhibiting tumor growth and angiogenesis [27]. Therefore, ATF peptide should represent a very good candidate for engineering multifunctional nanoparticles to target breast cancer.

The human epidermal growth factor receptor (EGFR) family includes EGFR (HER-1), EGFR-2 (HER-2), EGFR-3 (Her-3) and EGFR 4 (HER-4). The ligands that bind to EGFRs are divided into EGFR-like ligands such as EGF and TGF-α, and the heregulins. These ligands bind to EGFR monomers to promoter receptor dimerization and oligomerization, that ultimately results in the activation of the EGFR signaling pathway [29]. This EGFR signaling pathway plays a key role in the regulation of cell proliferation, survival and differentiation. As EGFR is one of the best studied ligand-receptor system and specific approaches for inhibition of EGFR signaling are currently among the most advanced and promising therapies currently undergoing preclinical and clinical studies [30-32].

It has been shown that 14 to 91% of human breast carcinomas express a high levels of the EGF receptors [33, 34]. About $10^6$ of EGFR are detected in a single breast cancer cell in vitro [35]. Overexpression of this receptor has been associated with highly aggressive breast cancer types and a poor response to therapeutic agents [34, 36, 37]. Prior preclinical and clinical studies have shown that blocking the EGFR via monoclonal antibodies or inhibition of EGFR tyrosine kinase with small molecule inhibitors inhibits the growth of breast cancers and sensitize chemotherapy responses [38, 39]. Although the efficacy of EGFR blocking monoclonal antibody has been demonstrated in clinical trials [40], the size of this antibody is very large (150-170 KDa) and is not ideal for efficient conjugation to nanoparticles. The large size of the intact antibody also limits the ability of the nanoparticle probes to diffuse from the vasculature into areas with tumor cells. In addition, the interaction of antibody with Fc receptors on normal tissues with an antibody can alter the specificity of tumor-targeted nanoparticles. To solve those problems, single-chain antibodies to EGFR that contain the specific EGFR binding region but lack the Fc region have been isolated from human scFv phage display libraries [41], and their inhibitory effects on tumor cell proliferation have already been shown in several laboratories [42, 43].

The present invention, among other things, explores and utilizes uPA, uPAR, and EGFR with other inventive aspects as set forth below, to detect and/or treat tumor, cancer and/or other diseases.

The present invention in one aspect provides a nanostructure. In one embodiment, the nanostructure comprises a nanospecies, a hydrophobic protection structure including at least one compound selected from a capping ligand, an amphiphilic copolymer, and combinations thereof, wherein the hydrophobic protection structure encapsulates the nanospecies, and at least one histidine-tagged peptide or protein conjugated to the hydrophobic protection structure, wherein the at least one histidine-tagged peptide or protein has at least one binding site.

FIG. 1 illustrates an exemplar embodiment of a nanostructure 100 according to the present invention. The nanostructure 100 includes, but not limited to, a nanospecies 102 having a hydrophobic protection structure 104 that encapsulates the nanospecies 102. The hydrophobic protection structure 104 includes a capping ligand layer 106 and/or a copolymer layer 108 (e.g., amphiphilic block copolymer). The following illustrative examples will use amphiphilic block copolymers, but other copolymers such as, but not limited to, amphiphilic random copolymers, amphiphilic alternating copolymers, amphiphilic periodic copolymers, and combinations thereof, may be used in combination with block copolymers, as well as individually or in any combination. In addition, the term "amphiphilic block copolymer" will be termed "block copolymer" hereinafter. Moreover, the nanostructure 100 has at least one histidine-tagged peptide or protein 110 conjugated to the copolymer layer 108. The at least one histidine-tagged peptide or protein 110 provides a binding site adapted for selectively binding to a cancer cell, a probe, or a therapeutic agent. The at least one histidine-tagged peptide or protein 110 includes a histidine-tagged amino-terminal fragment (ATF) of urokinase plasminogen activator (uPA), a histidine-tagged epidermal growth factor receptor (EGFR) single chain antibody (ScFv EGFR), or the like. The binding site of the at least one histidine-tagged peptide or protein can be at the C-terminal, N-terminal or inside of the peptide or protein between two functional domains on the peptide or protein.

Additionally, the nanostructure 100 can include, but not limited to, a bio-compatibility compound 112 and/or a probe 114. A probe 114 can be conjugated to the copolymer layer 108 or, alternatively, to a binding site of the at least one histidine-tagged peptide or protein 110 (not shown). One example of the bio-compatibility compound is a polyethylene glycol molecule having a molecular weight of about 500 Da to 50,000 Da.

In general, the nanostructure 100 can be formed in a manner described in FIGS. 2A through 2D. FIG. 2A illustrates the nanospecies 102 with the capping ligand 106 disposed on the nanospecies 102 and the block copolymer 108 disposed on the capping ligand layer 106 to form the hydrophobic protection structure 104. In one embodiment, the capping ligand 106 includes tri-octylphosphine oxide. FIG. 2B-2D illustrate the addition of at least one histidine-tagged peptide or protein 110 onto the hydrophobic protection structure 104 through the linkage of a chelating compound 111 to form the nanostructure 100. The following illustrative examples will use nickel-nitrilotriacetic acid (Ni-NTA) as the chelating compound III, but other chelating compounds may also be used to practice the present invention, individually or in any combination. The following illustrative examples will use a nanostructure with six (6) histidine-tagged peptides or proteins formed according to one embodiment of the present invention, each histidine-tagged peptide or protein providing a binding site adapted for selectively binding to a cancer cell or a probe. Nanostructures with other numbers of histidine-tagged peptides or proteins formed according to the present invention may also be used.

The nanospecies 102 is selected from a quantum dot, a metallic nanoparticle, and a metal oxide nanoparticle. The quantum dot comprises a core and a cap. In one embodiment, the core of the quantum dot is selected from the group consisting of IIA-VIA semiconductors, IIIA-VA semiconductors, IVA-IVA semiconductors, and IVA-VIA semiconductors. In another embodiment, the core of the quantum dot is selected from the group consisting of IIA-VIA semiconductors. In an alternative embodiment, the core of the quantum dot is CdSe. In one embodiment, the quantum dot is CdTe/CdSe. The cap is selected from the group consisting of IIA-VIA semiconductors of high band gap. In one embodiment, the cap comprises ZnS.

The amphiphilic copolymer is selected from amphiphilic block copolymers, amphiphilic random copolymers, amphiphilic alternating copolymers, amphiphilic periodic copolymers, and combinations thereof. In one embodiment, the amphiphilic copolymer is a block copolymer selected from a diblock copolymer, a triblock copolymer, and combinations thereof. The amphiphilic block copolymer includes an ABC triblock structure having grafted 8-carbon alkyl side chains, wherein the ABC triblock structure includes a poly-butylacrylate segment, a poly-ethylacrylate segment, and a poly-methacrylic acid segment. In one embodiment, the amphiphilic copolymer has a molecular weight of about 50,000 Da to 200,000 Da, preferably about 100,000 Da.

The nanostructure may also comprise a probe disposed on the hydrophobic protection structure, wherein the probe is selected from an antibody, a polypeptide, a polynucleotide, a drug molecule, an inhibitor compound, and combinations thereof.

Another aspect of the present invention relates to a method of synthesizing a multifunctional nanostructure for tumor imaging and treatment. In one embodiment, the method includes the following steps: at first, a nanospeices with a hydrophobic protection structure formed around the nanospeices that includes at least one compound selected from a capping ligand, an amphiphilic copolymer, and combinations thereof is provided. Then at least one histidine-tagged peptide or protein is conjugated to the hydrophobic protection structure, where the at least one histidine-tagged peptide or protein has at least one binding site. The conjugating step is performed with a chelating compound. The chelating compound comprises nickel-nitrilotriacetic acid (Ni-NTA). The nanospecies can be a quantum dot, and the hydrophobic protection structure includes a capping ligand and an amphiphilic copolymer. The amphiphilic copolymer includes an ABC triblock structure having grafted 8-carbon alkyl side chains. The at least one histidine-tagged peptide or protein includes a histidine-tagged amino-terminal fragment (ATF) of urokinase plasminogen activator (uPA), a histidine-tagged epidermal growth factor receptor (EGFR) single chain antibody (ScFv EGFR), or the like.

The method may further comprise the step of attaching a bio-compatibility compound to the hydrophobic protection structure. The bio-compatibility compound is a polyethylene glycol molecule. Other bio-compatibility compounds can also be used to practice the present invention.

The method may also comprise the step of attaching a probe to the hydrophobic protection structure or the at least one binding site of the at least one histidine-tagged peptide or protein. The probe is selected from an antibody, a polypeptide, a polynucleotide, a drug molecule, an inhibitor compound, and combinations thereof. In one embodiment, the probe comprises a drug, a therapeutic agent, a radiological agent, a molecule drug, and any combinations thereof.

Figure 3:
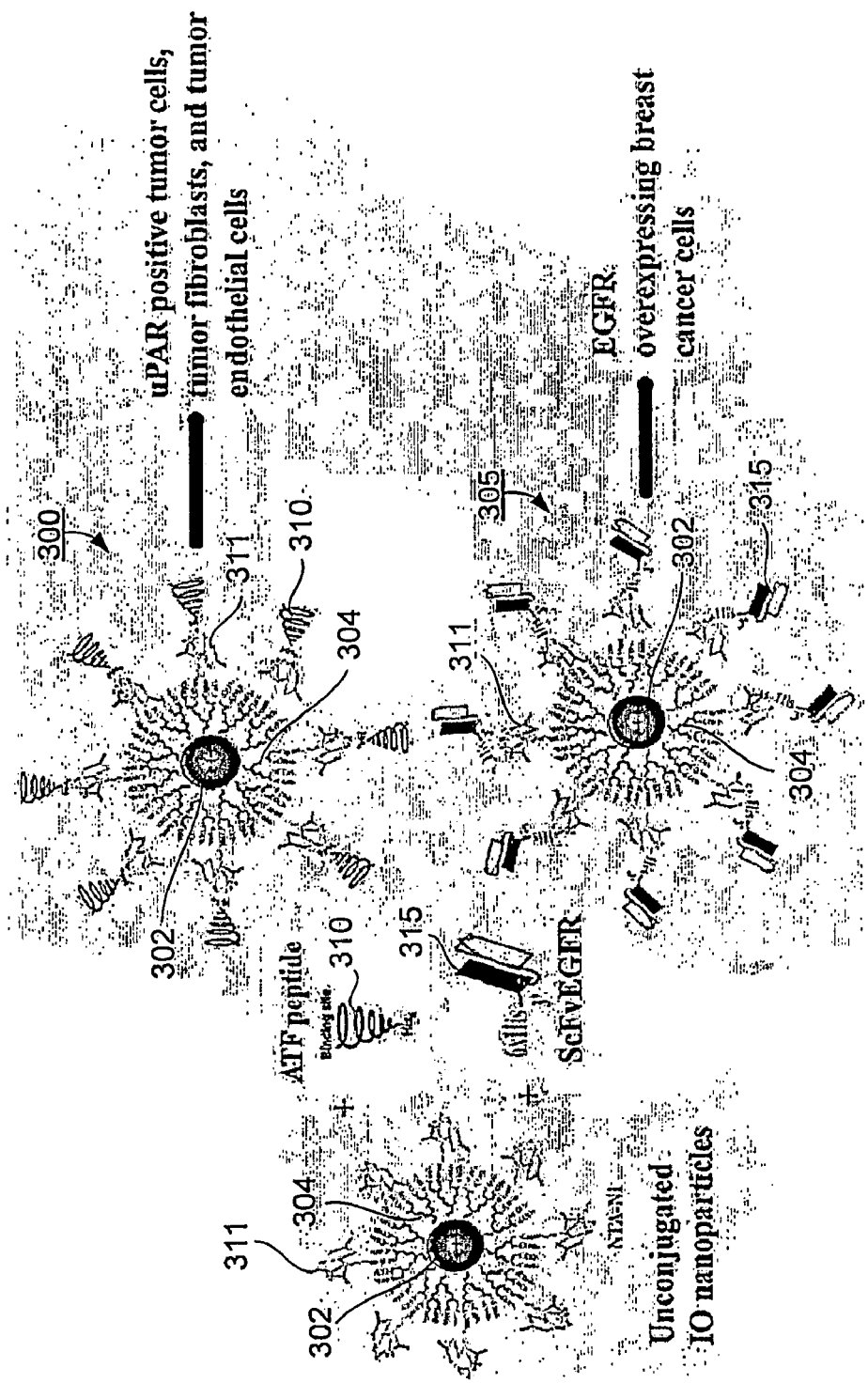
FIG. 3 shows schematically a multifunctional nanostructure according to one embodiment of the present invention.

Referring to FIG. 3, nanostructures according to embodiments of the present invention are shown. The nanostructure 300(305) has a superparamagnetic iron oxide (IO) nanocrystal 302. The IO nanocrystal has a nanosize detectable by magnetic resonance imaging (MRI). The nanostructure 300 (305) also has a protection structure 304 formed with an asymmetric dendrimer, where the protection structure 304 encapsulates the superparamagnetic IO nanocrystal 302. Furthermore, the nanostructure 300(305) includes at least one histidine-tagged peptide or protein 310(315) conjugated to the protection structure, wherein the at least one histidine-tagged peptide or protein 310(315) has at least one binding site. The binding site of the at least one histidine-tagged peptide or protein can be at the C-terminal, N-terminal or inside of the peptide or protein between two functional domains on the peptide or protein.

The nanostructure 300(305) further has a chelating compound 311 for conjugating the at least one histidine-tagged peptide or protein 310(315) to the protection structure 304. In the exemplary embodiment, the chelating compound 311 is nickel-nitrilotriacetic acid (Ni-NTA). Other chelating compounds can also be used to practice the present invention.

The dendrimer has particularly attractive properties that include stoichiometric distribution of functional groups, good water solubility and controllable size and molecular weight. Asymmetric dendrimmer has two types of terminal groups with different reactivity, providing bi-functions with a single molecule [60, 61]. Use of asymmetric terminal groups will allow one kind of terminal group, hydroxamate, to interact with the superparamagnetic IO nanocrystal on the core side of core-shell structure and the other set of hydroxide terminal groups to be exposed, allowing the introduction of multiple functional groups, such as carboxylate groups or hydroxyl groups that can be used to cross-link the "probe molecules" for target specific binding [60]. According to embodiments of the present invention, the asymmetric dendrimer is adapted for substituting small molecules of citrate on the surface of the superparamagnetic IO nanocrystal, which retains the superparamagnetic properties of the IO nanocrystal, but with the surface functionalized for conjugating the at least one histidine-tagged peptide or protein.

Additionally, the nanostructure 300(305) may also have a therapeutic agent coupled to the protection structure or the at least one binding site of the at least one histidine-tagged peptide or protein.

Figure 4:
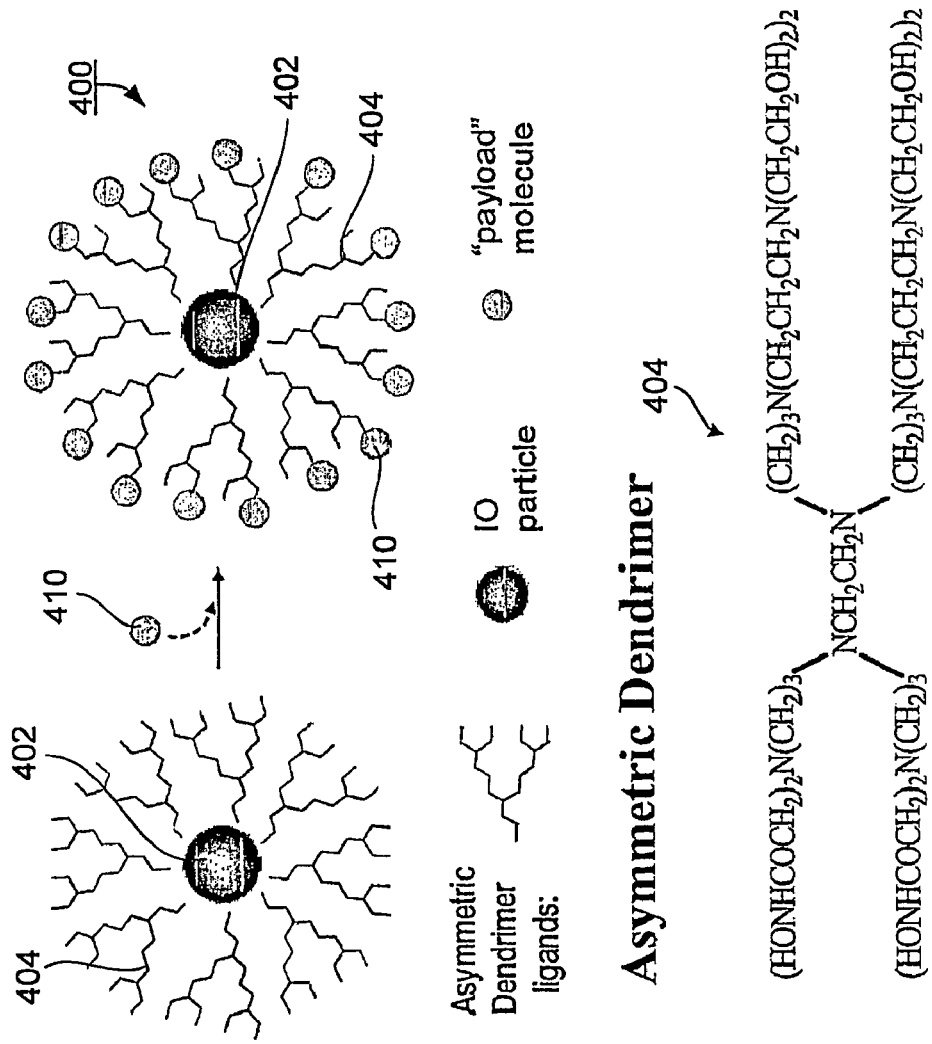
FIG. 4 shows schematically a procedure of synthesizing a multifunctional nanostructure according to one embodiment of the present invention.

FIG. 4 shows another nanostructure 400 according to one embodiment of the present invention. The nanostructure 400 has a monocrystalline IO 402 at a size of a few or more nanometers coupled with an asymmetric dendrimer 404. The coupled monocrystalline IO 402 is then conjugated with tumor targeting peptides or antibodies ("payload molecule") 410.

The present invention also provides a method of synthesizing the nanostructure having a superparamagnetic IO nanoparticles conjugated with histidine-tagged peptides or proteins. According to one embodiment of the present invention, the method includes the steps of (1) coupling Ni-NTA to —COOH side chain of the coating molecules of the IO nanoparticle; and 2) conjugating the histidine-tagged ATF-peptide or ScFv EGFR to the IO nanoparticles through Ni-NTA-carboxylate linker.

To obtain IO nanoparticles with surface activated —COOH functional groups, an asymmetric dendrimer molecules is used to substitute small molecule of citrate on the surface of the iron oxide particles, which retains the superparamagnetic properties of the IO nanoparticles, but with the surface functionalized for conjugating histidine-tagged peptides. A method reported by Wang et al. [60, 61] is adapted for preparation of the asymmetric dendrimer. After conjugating the asymmetric dendrimer to the core shell of the IO nanoparticles, the surface modified IO nanoparticles have hydroxamatic acid anchor groups at one end of dendrimer attaching to the IO nanoparticle —COOH groups then is be introduced to the other end and readily to be cross-linked to histidine-tagged peptide.

The histidine-tagged peptides comprise a histidine-tagged amino-terminal fragment (ATF) of urokinase plasminogen activator (uPA). In another embodiment, the at least one histidine-tagged peptide or protein comprises a histidine-tagged epidermal growth factor receptor (EGFR) single chain antibody (ScFv EGFR).

Although various methods have been used to conjugate peptides, antibodies and proteins to nanoparticles, one of the major problems faced in conjugation of targeting proteins or antibodies is that direct coupling of these proteins to QDs can not control the conjugation of QD to the selected amino acid residue of the protein due to the reaction of —COOH to —NH$_2$ can occur in multiple sites, thus, specific binding sites on the conjugated proteins may become blocked, due to being linked on or near the binding domain, significantly decreasing the tumor-targeting efficiency of nanoparticles.

Among other things, the invented methods and nanostructures have at least the following advantages compared to conventional methods: (1). Histidine-tag can be engineered at any locations on the protein, such as the C-terminal, N-terminal or inside of the protein between two functional domains. This indirect "his-tag" coupling method has advantages in directing the ligand to conjugate to the selected residue, resulting a compact overall probe sizes and improved specificity and binding efficiency. (2). The invented methods are very simple and efficient compared to other conjugation methods. Pre-conjugated QDs-Ni-NTA can be made as a commercial product and ready to be linked to any His-tagged peptide, proteins and antibodies just by mixing and incubating the QDs-Ni-NTA with histidine-tagged peptides or proteins following by an ultracentrifugation to separate conjugated-QDs from free peptides or proteins. (3). The tumor targeted QDs using ATF and ScFv EGFR have multi-functional nanoparticles, which have potential to be used for in vivo optical imaging of human cancer as well as a tumor targeted carrier for therapeutic agents. Since blocking uPAR or EGFR function using ATF or ScFv EGFR also inhibits tumor growth, metastasis and/or angiogenesis, those tumor targeted nanoparticles themselves are dual-function nanoparticles.

These and other aspects of the present invention are more specifically described below.

EXAMPLES

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Conjugation of Six His-Tagged Peptides or Proteins To QDs

To establish a simple and efficient method for conjugation of targeting peptides to QDs, a novel strategy that applies the principle in purification of His-tagged peptides is developed by utilizing the interactions between histidine and nickel molecules. Addition of six-histidines to a peptide or protein is a commonly used method in production and purification of recombinant proteins but no one suggested or even hinted to apply it for conjugating tumor targeting peptides, protein ligands or engineered antibodies to QD probes until the present invention was invented. The dissociation constant of 6×His-tagged protein to Ni-NTA has been measured to be $10^{-13}$, a value stronger than that for most antibody binding [62]. Moreover, the interaction of 6×His-tag with Ni-NTA has been shown to be stable and it is also virtually unaffected by high salt (up to 1 M), nonionic detergents (Triton X-100 or Tween-20 up to 1%), organic solvents, ethanol or glycerol to 30%, and reducing agents (up to 10 mM of mercaptoethanol) or highly denaturing conditions such as in the presence of about 8 M urea or about 6 M quanidine hydrochloride. Moreover, there were no major stability problems in recent studies of His-tagged gold nanoparticles [63].

A variety of high-quality quantum dots, such as CdSe, CdTe, and their alloys CdSeTe, with a size-tunable light emission from visible fluorescence to red-shifted emission up to 850 nm with yields up to 60%, have been synthesized by the inventors.

Figure 2:
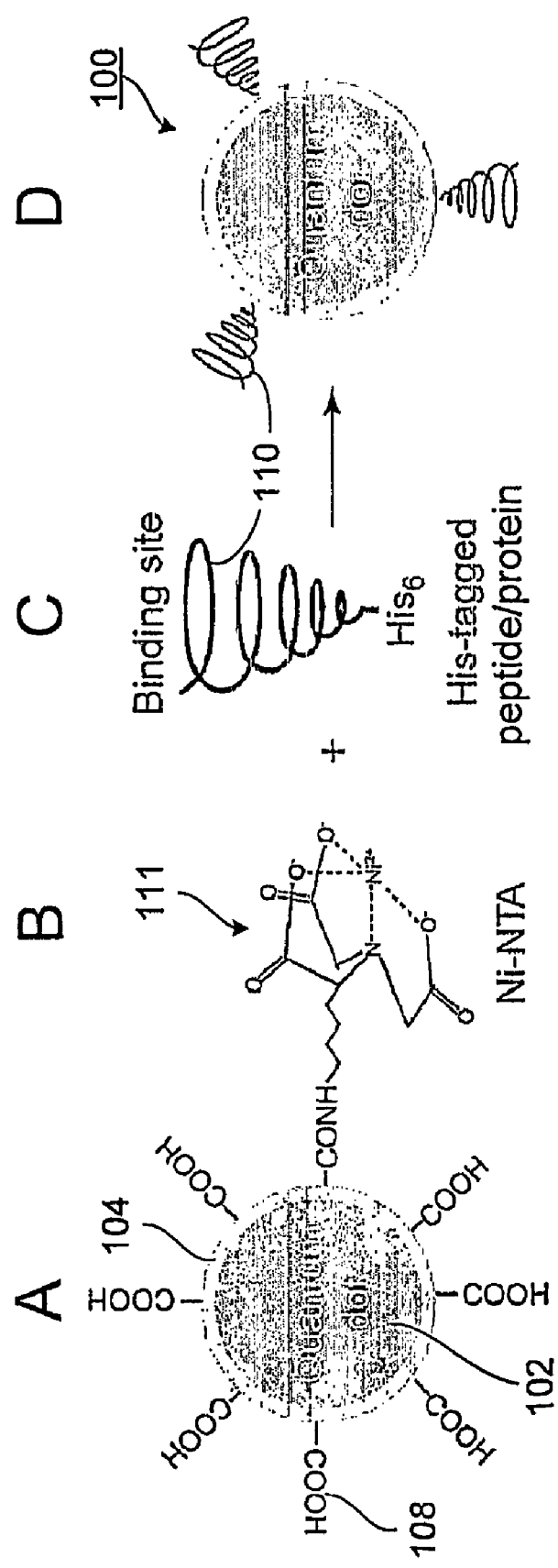
FIG. 2 shows schematically a procedure of synthesizing a multifunctional nanostructure according to one embodiment of the present invention.

In one embodiment, a high-molecular-weight (MW=100, 000 Da) copolymer with an elaborate ABC triblock structure and grafted 8-carbon alkyl side chains, as shown schematically in FIG. 2, is used to practice the present invention. The copolymer is a block copolymer, and the ABC triblock structure is made of A, B and C block segments each different from the others. Other types of copolymers, such as random copolymer, alternating copolymer, block copolymer, graft copolymer, star copolymers, and brush copolymers, can also be utilized to practice the present invention. Dynamic light scattering (DLS) measurements indicate that the assembled QD probes have a hydrodynamic radii of about 5-10 nm [1]. Targeting peptides are then linked to QDs using a chelating compound (nickel-nitrilotriacetic acid or Ni-NTA). A six Histagged green fluorescence protein (GFP) is produced to examine the stability of the His-tagged-protein-Ni-NTA-QD complex. It is found that the GFP-Ni-NTA-QD particles are very stable at room temperatures.

One of the major problems that conventional conjugation of targeting proteins or antibodies is faced is that direct coupling of these proteins to QDs can not control the conjugation of QD to the selected amino acid residue of the protein because the reaction of —COOH to —NH2 can occur in multiple sites, thus, specific binding sites on the conjugated proteins may become blocked, due to being linked on or near the binding domain, significantly decreasing the nanoparticle's tumor-targeting efficiency.

However, according to the present invention, six histidine-tagged peptides or proteins are conjugated to the QDs. Since the histidine-tag can be engineered to bind at any locations on the protein, such as the C-terminal, N-terminal or inside of the protein between two functional domains, this indirect "histidine-tag" coupling method has advantages in directing the ligand to conjugate to the selected residue, resulting a compact overall probe sizes and improved specificity.

After obtaining purified peptides and single chain antibodies, these peptides and antibodies are conjugated to different QDs. Although results from the preliminary study of the inventors indicate that His-tagged peptides or antibodies can be conjugated to QDs using a relatively simple procedure, several technical questions are still to be answered. First, the hydrophilic surface of the QD-COOH nanoparticles has 400 to 500 carboxylic acid groups. To determine the numbers of peptides or single chain antibodies coupled on each QD, His-tagged GFP protein is used to conjugate to orange-red QD at different ratios of QDs to GFP protein. Based on the values determined by measuring for the fluorescence intensity ratio of GFP and QDs with known quantum yields, the number of GFP protein on each QD is estimated. Then examining binding of the targeted QDs to tumor cells using QDs coupled with different amounts of the targeting peptides or single chain antibodies, to determine which coupling efficiency gives us a strong fluorescence signal while using an adequate amount of the targeting peptides. Although increasing the number of targeting peptides on QDs will enhance the binding affinity of the targeted QDs to tumor cells, an excessive amount of coupled peptides or single chain antibodies would increase the size of the particle and unnecessarily use up the targeting peptide. The additional —COOH side groups on the targeted QDs may be used for further conjugation of other therapeutic molecules such as apoptosis-inducing peptides or chemotherapy drugs. Using the same GFP-coupled QDs, one may determine the stability of the link between His-tagged protein and Ni-NTA-QDs at different storage conditions. The amount of coupled GFP and free GFP can then be measured at different time points, to determine stability of the targeted QDs. The specificity and affinity of the targeted QDs after storage can also be examined in vitro on tumor cell lines.

In one embodiment, the targeted peptides is conjugated to near-infrared (NIR) QDs. Although the chemical composition of ternary alloyed NIR QDs are different from that of the traditional QDs with visible fluorescence, The same triblock copolymers is used to modify the surface of these NIR QDs, so that the His-tagged targeting peptides can be conjugated to NIR QDs using the same procedure.

In one embodiment, the human or mouse ATF peptides and ScFv EGFR is conjugated to red or NIR QDs through Ni-NTA. To determine the specificity of targeted human ATF-QDs, human breast cancer cell lines MDA-MB-231 and MDA-MB-435, which express high levels of uPAR, is used. A normal immortalized human mammary epithelial cell line (MCF-10A) can be used as a negative control. The specificity of mouse ATF-QDs can be examined in mouse mammary tumor 4T1 cells. A mouse fibroblast cell line derived from uPAR deficient mice is used as a negative control (Provided by Dr. Mieke Dewerchin, Vlaams Interuniversitair Institut Biotechnologie, Leuven, Belgium). The specificity of ScFv EGFR-QDs is examined in breast cancer cell lines MDA-MB-231 and BT 20 (EGFR+), and a control cancer cell line MDA-MB-435 (EGFR−), as well as a normal human mammary epithelial cell line MCF-10A and a normal primary fibroblast cell line, HDF. The results is examined using an inverted Olympus microscope equipped with a digital color camera, a broad band light source and Spex 270M spectrometer/imaging spectrograph system that is able to detect fluorescence signals with an emission wavelength up to 1000 nm.

In addition, increasing evidence indicates that both EGFR and uPAR are internalized after binding to their ligands [67-69], which is an advantage for the enhancement of imaging signals and sensitivity of cancer detection, as well as for use as targeted delivery vehicle for therapy agents. For example, it has been shown that ATF-recombinant toxins are able to be internalized into uPAR-expressing tumor cells, producing specific cytotoxic effects [68]. In this study, whether ATF- or ScFv-EGFR targeted QDs can be internalized into breast cancer cell lines that express the receptors is examined. The breast cancer cell line MDA-MB-231, which expresses high levels of both uPAR and EGFR, is incubated with either human ATF- or ScFv EGFR-QDs for 1, 3, 6, and 24 hrs. The negative controls are human fibroblast and breast cancer MDA-MB-435 (EGFR−), or the normal human mammary epithelial cell line MCF-10A (uPAR−). The cells are washed and fixed at different time point. Internalization of the QDs can be determined using a confocal microscope. In a previous study, the inventors found that even without targeting and internalization moieties, some QDs were taken into living cells after a long time incubation (>24 hr). However, results related to the present invention suggest that ligand-mediated specific internalization is faster and stronger than non-specific internalization. Furthermore, QDs can be incubated with the cells in the presence or absence of un-conjugated ATF peptides or ScFv EGFR. A reduced amount of intracellular QD in the presence of un-conjugated peptides suggests that the internalization is mediated by specific interactions between the ligands and their receptors.

Example 2

Evaluation of Molecular Targets for Engineering/Synthesizing Multifunctional Nanostructures To identify molecular targets for use in engineering/synthesizing dual functionality nanoparticles for both tumor imaging and inhibiting tumor growth, certain tumor markers for breast cancer have been examined. Several criteria are used to select the targeting molecules, such as high expression in most breast cancers but low levels in normal tissues, and whether the marker plays an important role in the proliferation and progression of tumor cells. It has been shown that uPAR and EGFR are good molecular targets for production of the multifunctional probes. Several other tumor markers are also potential good molecular targets, such as Her-2/neu. Indeed, although Her-2/neu expression is more specific for breast cancer cells as compared with uPAR or EGFR, only 20-30% of invasive breast cancer tissues are positive for Her-2/Neu expression, which may affect tumor imaging sensitivity as well as effectiveness of anti-tumor therapy.

Figure 5:
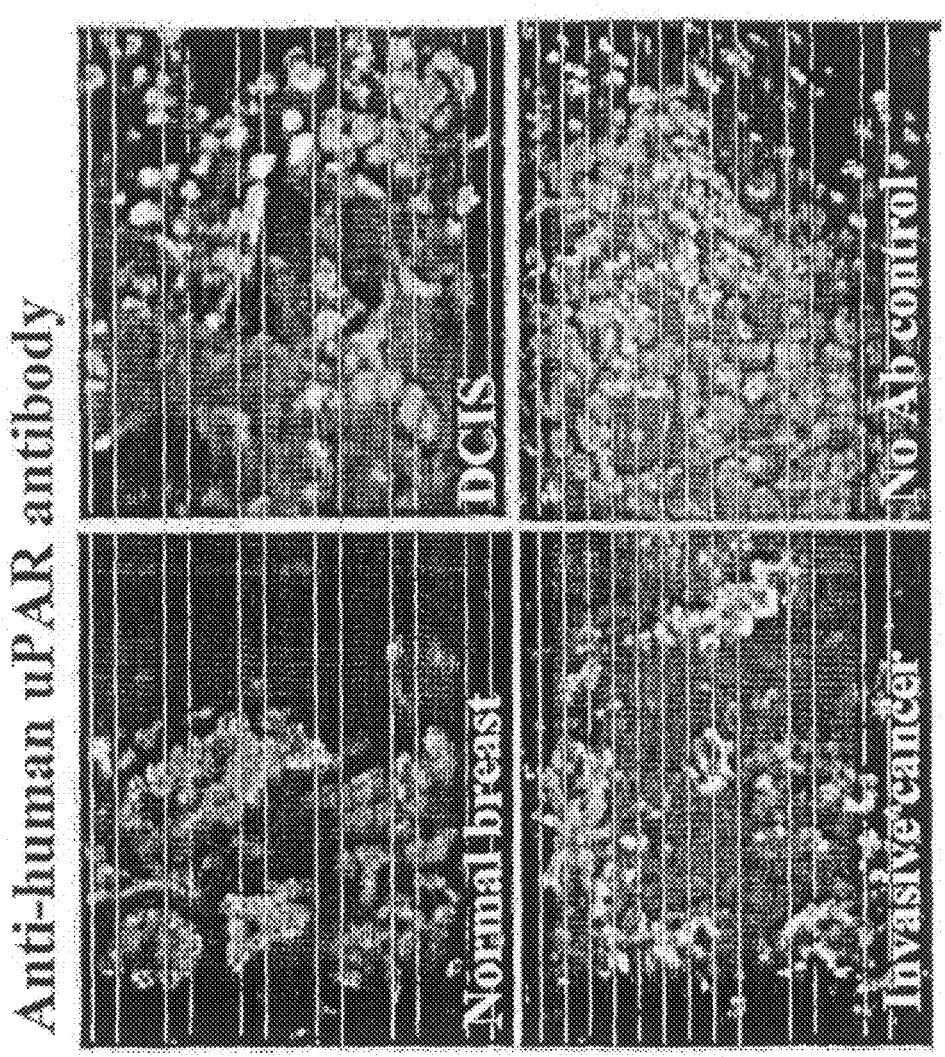
FIG. 5 shows images of upregulation of uPAR human breast cancer tissue using immunofluorescence labeling.

The uPAR marker is highly expressed in many human tumor cells, intratumoral fibroblasts and tumor endothelial cells [23] and more particularly, uPAR is detected in over 90% of human breast carcinoma tissues [23]. Using immunofluorescence labeling with an anti-human uPAR antibody, it is found that the level of uPAR expression is very low or absent in normal human breast tissues, while a high level of uPAR is detected in breast cancer tissues at all stages including the early stage of breast cancer (DCIS), as shown in FIG. 5.

Figure 6:
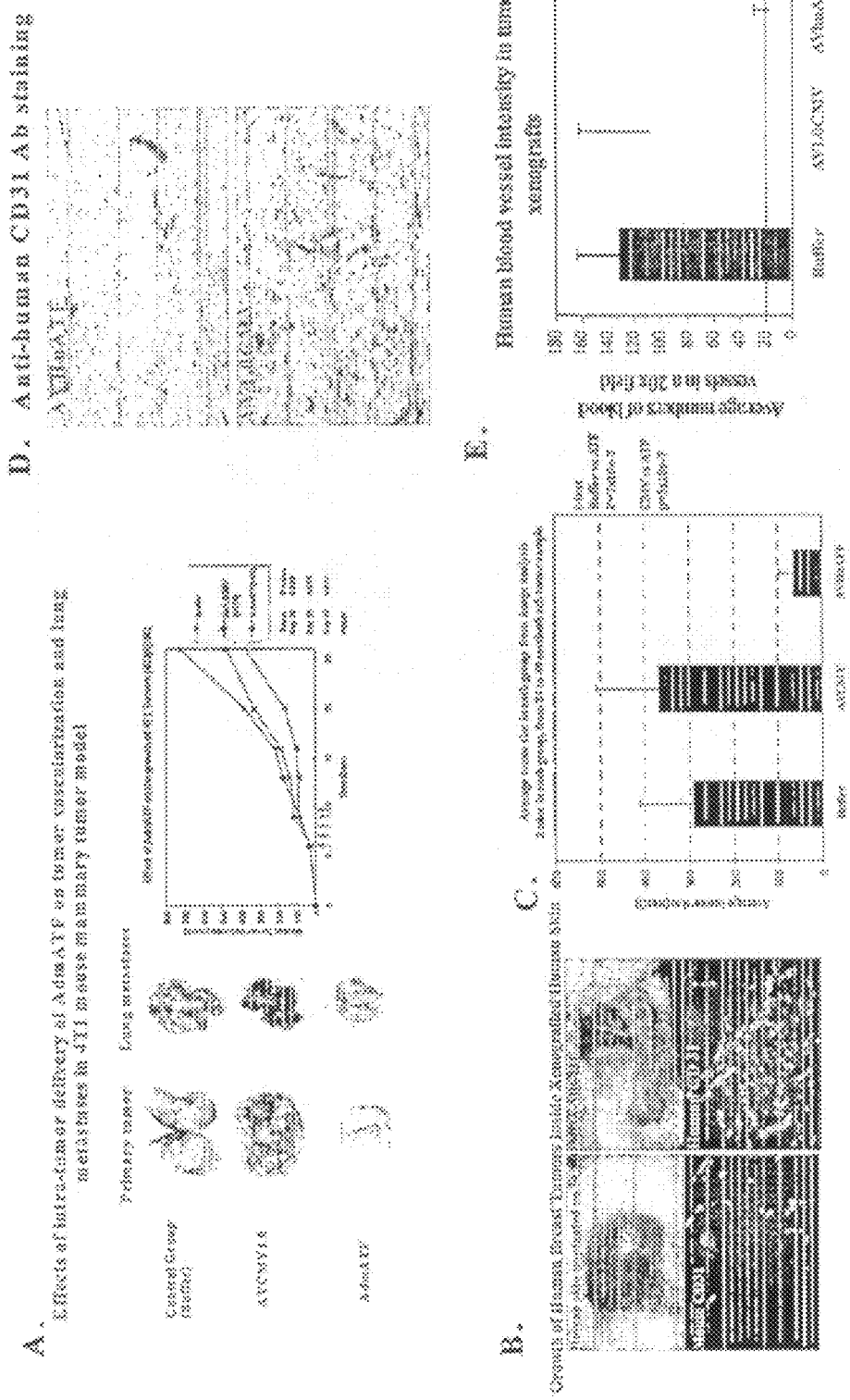
FIG. 6 shows effects of expression of mouse or human ATF fragments by adenoviral vectors on inhibition of tumor growth and angiogenesis in a mouse mammary 4T1 tumor model and in a human breast cancer model xenografted in chimeric human skin/SCID mice. (A) Expression of Mouse ATF fragments inhibited the growth of mouse mammary 4T1 tumor, reduced blood vessels and decreased lung metastases. (B) Establishment of human breast xenograft model in a chimeric human skin/SCID mouse. Over 70% of blood vessels were derived from a human origin as determined by immunofluorescence labeling with an anti-human CD31 antibody. (C) Expression of human ATF fragments by adenoviral vectors significantly inhibited the growth of human breast cancer MDA-MB-231 cells in the human skin xenograft. (D) and (E) Expression of human ATF fragments by adenoviral vectors reduced the blood vessel intensity in the tumors.

In addition to the benefit of having a high level of expression of the uPAR target on the cell surface, several studies have shown that blocking of the uPAR function with a non-catalytic ligand (ATF) or small peptides can inhibit tumor growth and angiogenesis. Since binding of uPA, from which the ATF is derived, to uPAR has species specificity, the effects on tumor growth of adenoviral vectors expressing either mouse ATF or human ATF on tumor growth have been examined in a mouse mammary 4T1 tumor model in Balb/c mice and a human skin chimeric/breast cancer xenograft model in SCID mice. It is found that intratumoral injection of adenoviral vectors expressing the mouse ATF significantly inhibited the growth of primary and lung metastasis in the 4T1 tumors, as shown in FIG. 6A. To determine the effect of expression of the ATF fragments on human tumor cells as well as angiogenic human endothelial cells, a chimeric human skin/SCID mouse model has been established. After transplanting human skin into SCID mice for 3 weeks, over 70% of blood vessels in the skin xenograft were of a human origin, as determined by immunofluorescence labeling using either anti-human CD31 or mouse CD 31 antibodies, as shown in FIG. 6B. By using adenoviral vectors expressing a human ATF fragment, it is found that intratumoral injection of the adenoviral vectors inhibited tumor growth, as shown in FIG. 6C, and reduced the number of tumor vessels in human breast cancer xenografted in the chimeric human skin/SCID mice, as shown in FIGS. 6D and 6E, human vessels were determined using an anti-human CD 31 antibody).

Example 3

Production of Mouse ATF-QD and Examination of the Specificity of the Targeted QD Nanostructure From the previously mentioned study, it is demonstrated that uPAR is an excellent molecule for targeting of engineered multifunctional nanoparticles. The inventors also used the same ATF protein sequence that was tested in the adenoviral vectors to produce His-tagged ATF peptides for use in engineering the ATF-QDs. Since binding of the ATF peptide to uPAR is species specific, mouse ATF peptides is selected first to study the feasibility of using ATF-QDs for tumor imaging in 4T1 mouse tumor model. A major advantage of using mouse ATF peptides is that the specificity and sensitivity of the ATF-QDs in detecting tumors can be precisely measured, since uPAR-expressing cells in a tumor mass include tumor cells as well as tumor endothelial and intratumoral stromal cells, which originate from the mouse. Nanoparticle imaging probes that can target not only tumor cells but also the tumor's vessels and stromal cells should increase the sensitivity of cancer detection. Additionally, the specificity and tissue distribution of the mouse of targeted ATF-QDs after systemic delivery into mice can be determined.

Figure 7:
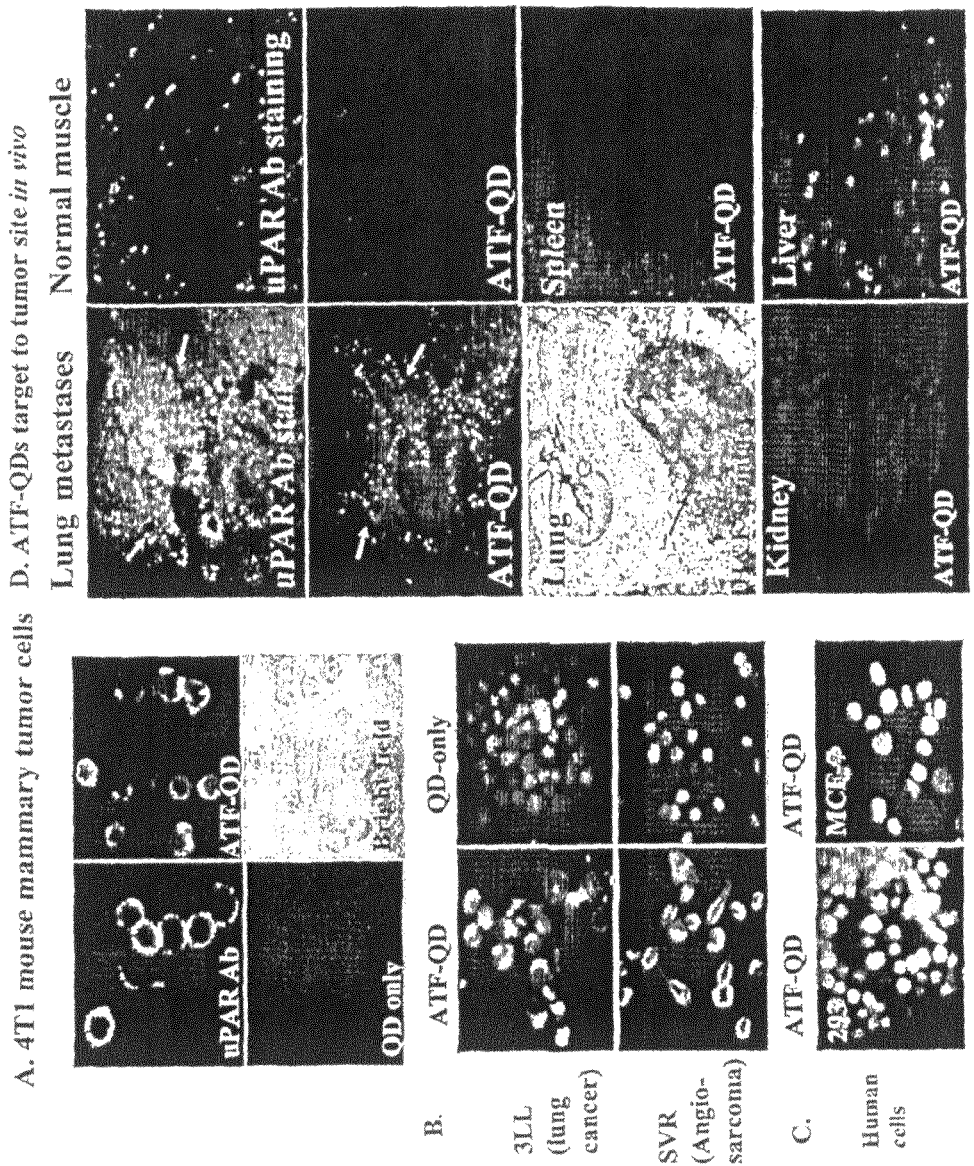
FIG. 7 shows the specificity of mouse ATF-QDs in mouse tumor cell lines and a mouse tumor model. (A) 4T1 tumor cells express a high level of uPAR as detected by uPAR antibody labeling. The targeted ATF-QDs, but not non-targeted QDs, produce a red fluorescence signal in 4T1 tumor cells. (B) Targeted ATF-QDs also generate strong fluorescent signals in mouse lung cancer (3LL) and angiosarcoma (SVR) cell lines. (C) Human embryonic kidney 293 and breast cancer MCF-7 cells are negative for mouse ATF-QD labeling. Lack of fluorescence labeling in human cells further indicates that the fluorescence image observed in mouse cells is not due to non-specific binding of ATF-QD to the cell surface since ATF binding is species specific. Human 293 and MCF-7 cells do have a low level of uPAR gene expression. (D) In vivo targeting of 4T1 tumor cells in lung metastases after systemic delivery of mouse ATF-QDs. 4T1 cells were injected i.v. for 2 weeks. ATF-QDs were then injected i.v. for 2 hrs. The major murine organs were frozen and frozen sections were examined for the presence of the ATF-QD-fluorescent signal in the lung metastases. As shown, ATF-QD fluorescent signal is detected in metastatic 4T1 tumor cells in the lung (yellow arrows). ATF-QD positive areas are co-localized with uPAR-positive tumor cells in the lung as detected by double-labeling the section with uPAR antibody (green). On the other hand, ATF-QD fluorescence is absent from normal muscle tissues, as it is also negative for uPAR antibody staining. A image of H&E staining shows the tumor areas in the lung under a 10× lens (black arrows). Furthermore, the ATF-QDs are not detectable or weak in liver and kidney tissue sections. However, a low level of ATF-QDs fluorescence is detected in spleen.

The gene construct for mouse ATF-fragment (1-135 aa) is cloned into a pET bacteria-expression plasmid and produced the His-tagged ATF peptides in *E. coli*. The His-tagged ATF peptides were purified using a Ni-protein purification column, then conjugated to the Ni-NTA functionalized QDs. The specificity of the mouse ATF-QDs was first examined in vitro in mouse tumor cell lines, where it is found that ATF-QDs incubated with live mouse tumor cells produced a strong fluorescence signal in those cells expressing high levels of uPAR, such as mouse mammary 4T1 and 3LL lung carcinoma cells. Bright fluorescence was also detected in a mouse angiosarcoma cell line SVR, which was derived from a mouse endothelial cell line, MS1 [64], as shown in FIGS. 7A and 7B. Since mouse ATF has a low affinity with human uPAR, mouse ATF-QDs doesn't produce fluorescence in either normal human cell line 293 or the human breast cancer cell line MCF-7, as shown in FIG. 7C.

The specificity of the mouse ATF-QDs has been examined in vivo, in a mouse mammary 4T1 tumor model. The 4T1 tumor model is a well-characterized spontaneously metastatic mammary tumor model, where subcutaneous injection of the 4T1 cells leads to the growth of primary and metastatic tumors in the lung, liver, spleen and bone within 4 weeks [65]. After injection of mouse ATF-QDs through the tail vein for 2 hrs, it is found that they selectively target the metastatic lesions in the lung, derived from the mouse mammary 4T1 tumors (FIG. 7D). It is found that strong ATF-QD-generated fluorescence (Red) in the lung metastatic lesions that were also positive for uPAR antibody staining (Green). On the other hand, very low levels of fluorescence was detected in the liver, kidney and muscle tissues (FIG. 7D). However, the ATF-QD fluorescence signal was found in the spleen, although much weaker than the tumor lesion's fluorescence (FIG. 7D). It is examined the feasibility of using ATF-QDs for in vivo tumor imaging. Following the 2 hr i.v. injection of ATF-QD, the mouse was placed under a micro-illumination system equipped with a CCD camera, designed specifically for detecting fluorescence images of small animals. However, results of the pilot study suggest that it is difficult to detect fluorescence signals produced in lung metastases by using this type of QD, which produces visible fluorescence at an emission at wavelength of 625 nm. To increase the sensitivity of the detection, it may need a better detection system, such as the combination of a wavelength-resolved spectral imaging system with Spectral unmixing algorithms software, which allows separation of autofluorescence spectra from the QD spectra, thus enhancing the signal to background ratio (Cambridge Research & Instrumentation, Inc., MA). Additionally, the development of near infrared (NIR) QDs is currently undergoing in Dr. Nie's lab, it is expected that NIR QD will enhance the sensitivity of imaging tumors in vivo. Therefore, this new QD system can then be tested in the present experimental model.

Example 4

Figure 8:
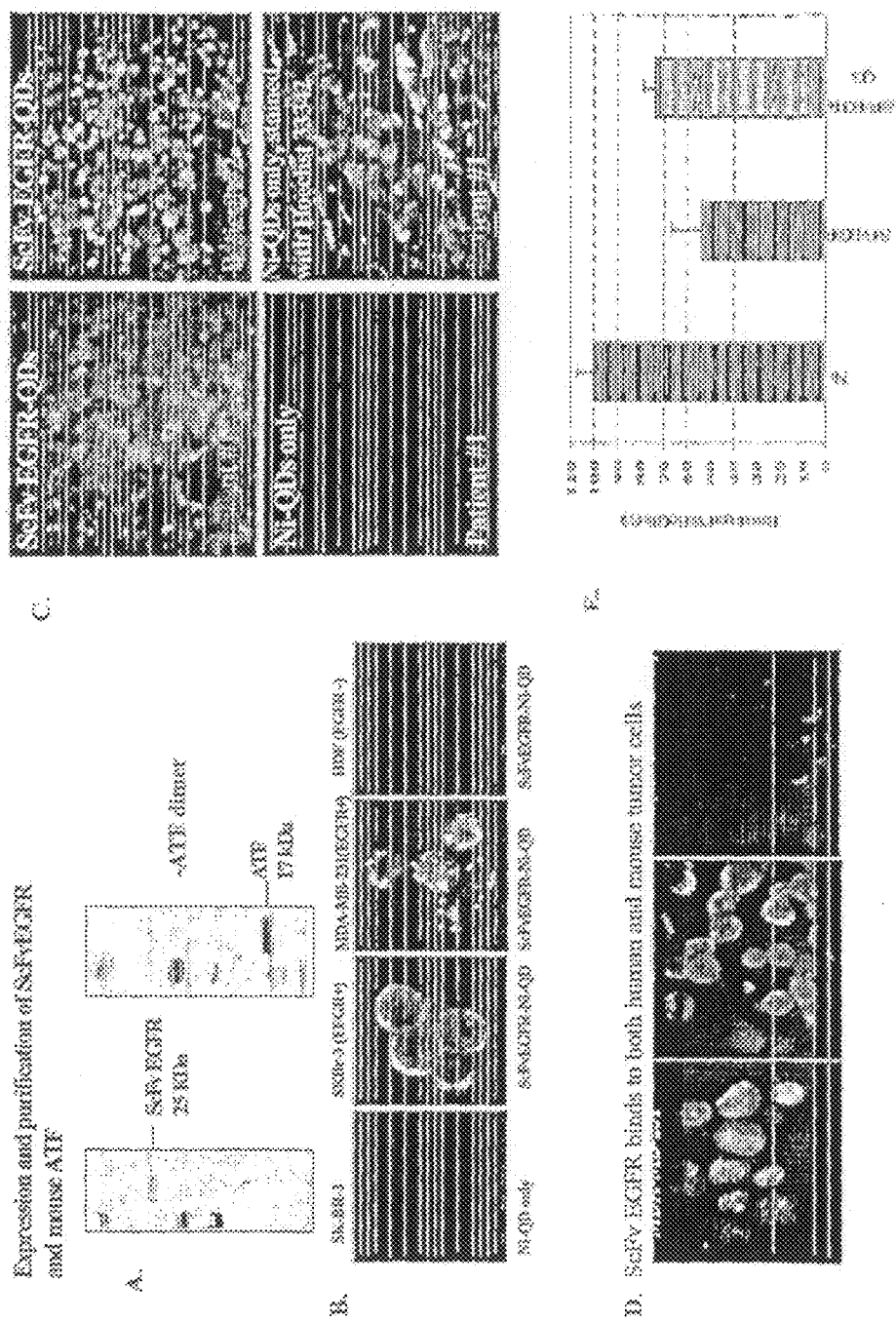
FIG. 8 shows the specificity of ScFv EGFR-QDs in human breast cancer cells and tissues as well as in mouse mammary tumor 4T1 cell line. (A) Production and purification of ScFv EGFR or mouse ATF in the pET bacteria expression system. (B) ScFv EGFR-QDs specifically bind to EGFR expressing breast cancer cells (viable cells). Specific internalization of the QDs, are seen in the NDA-MD-231 cells. Cell nuclei are counterstained with Hoechst 33342 (blue). (C) ScFv EGFR-QDs detect EGFR expressing breast cancer cells in frozen tissues obtained from two patients with invasive breast carcinomas. (D) ScFv EGFR single chain antibody also cross-reacts with the mouse mammary tumor 4T1 cells. (E) About 25 to 46% of the growth inhibition is found in MDAMB-231 cells after incubation with ScFv EGFR or ScFv EGFR QDs.

Production of ScFv EGFR-QDs and Examination of the Specificity of the Targeted QDs in Human Breast Cancer Cell Lines and Tissues It is well established that EGFR is highly expressed in many breast cancer cells and inhibition of EGFR receptor function prevents breast cancer cell growth. Therefore, it is possible that targeting QDs to EGFR may allow tumor imaging, as well as produce an anti-tumor effect. At present, single chain antibodies to EGFR that contain a specific EGFR-binding region but lack the Fc region have been isolated from human ScFv phage display libraries. A construct was obtained from Dr. Gregory P. Adams in the Fox Chase Cancer Center, PA, that produces a His-tagged anti-human EGFR single chain antibody (ScFvEGFR). Large amounts of this ScFv EGFR have been produced, using a pET bacteria expression system, and purified the resulting protein with a Ni-column, as shown in FIG. 8A. His-tagged ScFv EGFR was then conjugated to the QDs using Ni-NTA as described previously. To determine the specificity of ScFv EGFR-QDs, ScFv EGFR-QDs was incubated with viable breast cancer MDA-MB-231 and SKBr-3 cells (EGFR+) or human fibroblasts HDF (EGFR−) for 1 hr. It is found a strong fluorescence signal in the breast cancer cells but not in human fibroblasts (HDF), as shown in FIG. 8B (QDs producing green fluorescence were used for this study). It is further examined the specificity of ScFv EGFR QDs in breast cancer cells on frozen sections of human breast cancer tissue biopsies, demonstrating that ScFv EGFR-QDs are able to bind to human breast cancer cells and produce a strong fluorescence signal, as shown in FIG. 8C. Two out of three breast cancer tissues examined were strongly positive with ScFv EGFR-QD labeling.

Since the sequence of human and mouse EGFRs share 74% homology (NCBI, Genbank), it is examined whether this human ScFv EGFR also binds to mouse EGFR by labeling mouse 4T1 cells with and without the human ScFv EGFR single chain antibody, followed by a biotinylated mouse anti-His tag antibody and Texas-red-avidine. The EGFR single-chain antibody cross-reacts with mouse EGFR, although the fluorescence intensity is slightly weaker than that observed in human breast cancer MDA-MB-231 cells, as shown in FIG. 8D. It is also found that blocking EGFR function by ScFv EGFR inhibits cell proliferation of MDA-MB-231 cells, as shown in FIG. 8E Example 5

Establishment of Optical Imaging Method for Detection of QD Signals in Vivo

Figure 9:
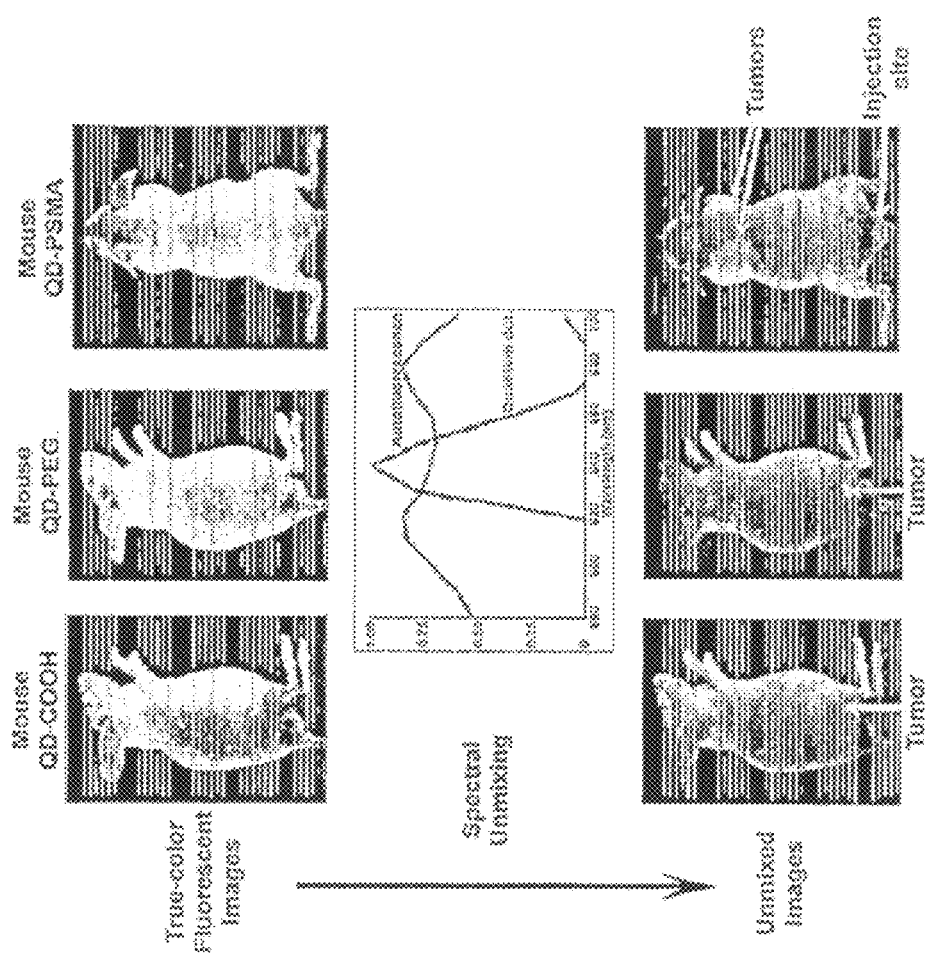
FIG. 9 shows in-vivo fluorescence images of tumor-bearing mice using QD probes with three different surface modifications. Carboxylic acid groups (left), PEG groups (middle), and PEG plus PSMA antibody (right). For each surface modification, a color image (top), two fluorescence spectra from QD and animal skin (middle), and a spectrally resolved image (bottom) were obtained from living mouse models bearing human prostate cancer of similar sizes.

Technology for optical imaging using tumor-targeted QDs has been established by the inventors. Systemic delivery of QDs conjugated with an anti-prostate specific membrane antigen (PSMA) antibody produced an optical image in xenografted prostate cancers in nude mice by using a whole body spectral imaging system that utilizes computer software to subtract the autofluorescence spectra, therefore, enhancing the QD spectra. As shown in FIG. 9, a mouse injected with non-targeted QD-COOH particles did not produce fluorescence in the xenografted tumor. Non-targeted QD-PEG particles only showed a weak fluorescence. However, the targeted PSMA antibody-QDs produced a strong fluorescence signal in the xenografted prostate cancers [1]. This technology can be utilized to image the targeted QDs produced for the breast cancer studies in mice.

Example 6

Superparamagnetic IO Particles and Functionalizing the Surface

Figure 10:
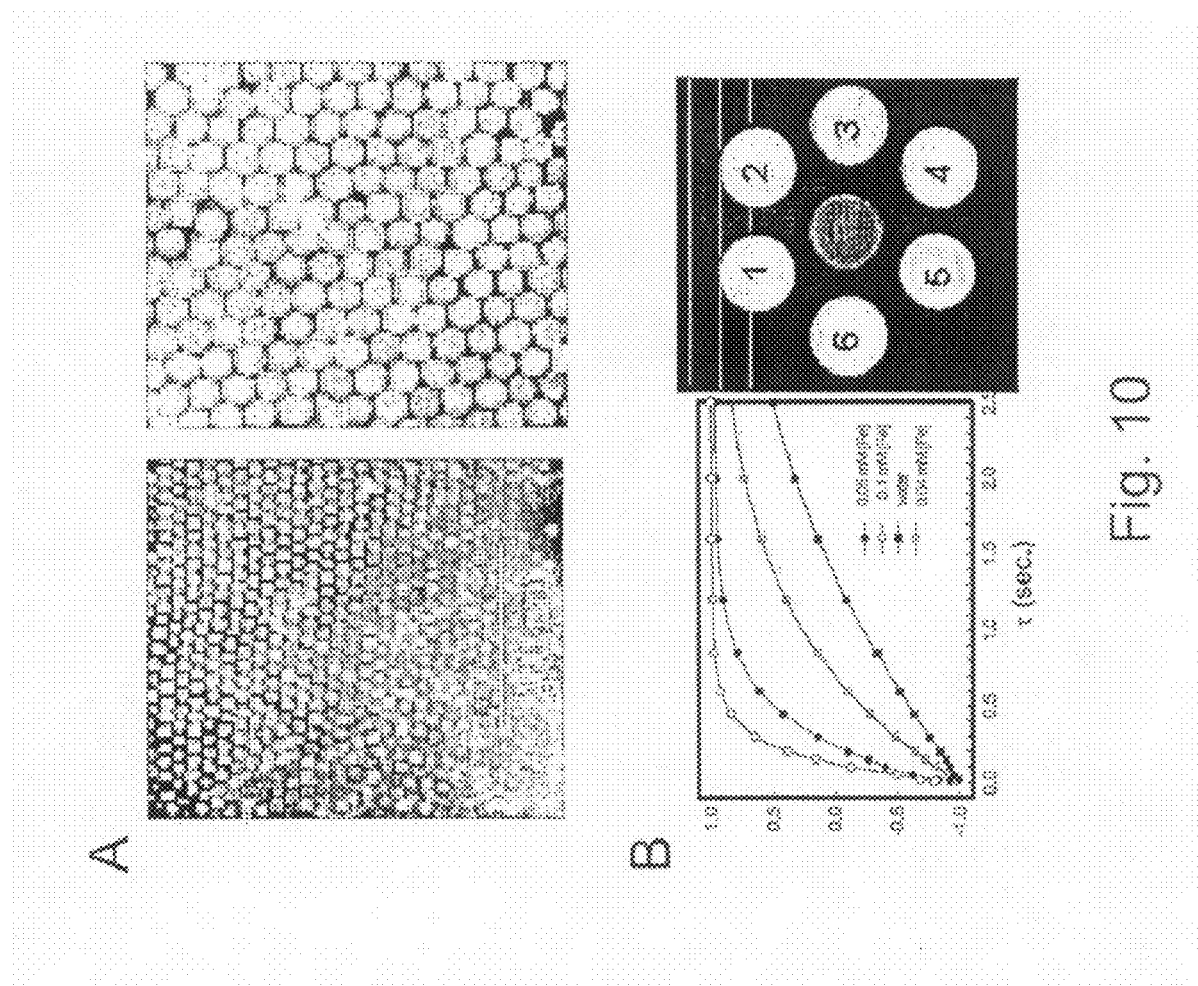
FIG. 10 shows (A) TEM images of IO nanoparticles having a core size of about 5 nm and an uniformed size distribution according to one embodiment of the present invention, and (B) $T_1$ relaxation times of IO nanoparticle aqueous solutions in different [Fe] concentrations (at 1.5T) measured by the inversion recovery method, and a spin echo image showed the contrast effect is dependent on IO nanoparticle concentration. Water is at the center. Gd-DTPA is 6. IO nanoparticle concentration increases from 1 to 5.

Although paramagnetic iron oxide particles have been used as an MRI contrast agent in recent years, its application is very limited. Recent works have shown that superparamagnetic iron oxide nanoparticle can be used for magnetic cell labeling for cellular imaging [55] and surface coating of IO nanoparticles will allow the introduction of functional groups that can be used for bioconjugation. Nevertheless, only a few studies were done to improve the quality of magnetic particles such as their size distribution, shape and surface coating. Recently, a new generation of superparamagnetic iron particles that have about 4-5 nm uniform sizes has been developed by the inventors and this type of IO nanoparticles can be further functionalized through surface coating of the asymmetric dendrimer which can be derivatized to provide functional groups for conjugating tumor targeting biomolecules such as peptides or antibodies [66]. Asymmetric dendrimer has been shown to have improved anti-hydrolysis when compared to the traditional single chain ligands, so it can survive hydrolysis under physiological conditions, when applied to a living system. Asymmetric dendrimer has a readily reactive surface for introducing multiple functional groups including carboxylate group that can be used to cross-link the "probe molecules" for target-specific binding [58]. The presence of carboxylate groups on the IO particles allows coupling of Ni-NTA and His-tagged peptides to IO nanoparticles to obtain a target specific MRI probe. The superparamagnetic IO ($Fe_3O_4$) nanocrystal are proved to be stable in the physiological conditions and has been applied to magnetically label various cell lines for in vivo imaging of cell trafficking. Transmission electron microscopy (TEM) shows that such superparamagnetic IO nanocrystals have an average size of about 5 nm within very narrow size distribution, as shown in FIG. 10A. Using an inversion recovering pulse sequence for $T_1$ measurement and a Carr-Purcell-Meiboom-Gill pulse sequence for $T_2$ measurement, the IO nanoparticle preparation has strong paramagnetic $T_1$ and $T_2$ shortening effect with R1 (e.g., $1/T1$)=27 $mM^{-1}s^{-1}$ and $R_2$ ($1/T_2$)=70 $mM^{-1}s^{-1}$ at 1.5T, respectively. FIG. 10B illustrates the substantial T1 changes in superparamagnetic IO nanoparticle solution compared to that of water. Interestingly, those IO nanoparticle also demonstrated wide range of MRI contrast effects in $T_1$, $T_2$ and $T_2$*(or susceptibility effect). The MRI contrast is a function of IO nanoparticle concentrations (shown in the series of spin echo images (FIG. 10B) of a set of phantom tubes containing IO particle solutions with different [Fe] concentrations ranging from 0.05 mM (#1) to mM (#5). This contrast effect is comparable to that of a 1% Gd-DTPA solution (#6). However, signal dropout and significant line broadening was observed (#5), attributed to signal dephasing due to the strong localized susceptibility effect $T_2$* effects induced by the paramagnetic IO particle when the particle concentration increases further.

Example 7

MRI Tumor Imaging in Mouse Xenograft Models

Figure 11:
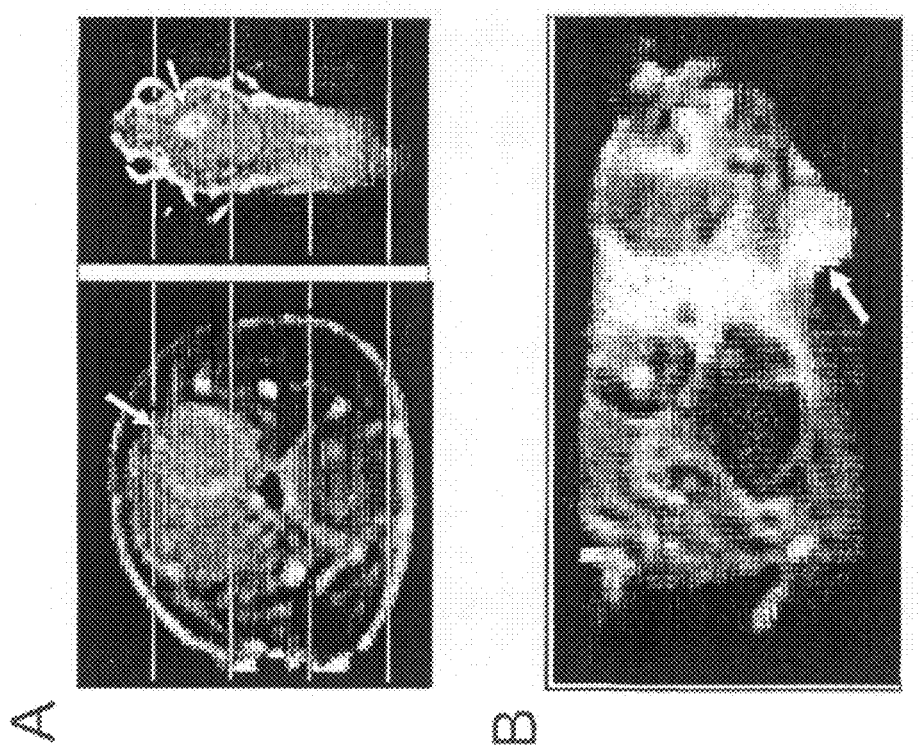
FIG. 11 shows MRI images of tumors growing in rats and mice.

In addition to the application of such superparamagnetic 10 nanaoparticles for cell labeling and cell tracking, the IO nanoparticles can also be applied as the blood pool contrast agent for delineating tumor boundary in vivo. T1 weighted contrast enhancement can be used to investigate xenografted rat brain tumor and human tumor in nude mice using T1 weighted MRI, as shown in See FIG. 11. As shown, injection of non-targeted monocrystalline iron oxide nanoparticle (MION) enhances MRI imaging of rat brain tumor and human tumor xenografted in nude mice. At present, the MRI technology for tumor imaging in small animals has been well established in Dr. Mao's laboratory and Fredrick Philips MRI Center at Department of Radiology at Emory University. The same technology can be used for imaging the targeted IO nanoparticles to detect and/or treat breast cancer.

Example 8

Examination of the Specificity of the Targeted IO Nanoparticles In Vitro

Figure 12:
FIG. 12 shows a TEM image of c-MION labeled cells indicated cellular compartmentalization of iron oxide particles (arrows indicated) clustered in the cytosol.

The results from in vitro study showed that IO naoparticles can be internalized by the various cell lines including insulin secreting bTC-3 cells and T-cells [55] as shown in FIG. 12, resulting magnetically labeled cells to be MRI sensitive. Even the sample with 0.1% labeled cells can be distinguished using MRI at 1.5T. The ability of the targeted IO nanoparticles is expected to be actively internalized by tumor cells should greatly increase the sensitivity of tumor imaging. Moreover, this imaging 10 nanoparticle can also serve as a carrier to bring the therapeutic agents into the tumor cells. The target specific IO nanoparticles should be internalized in the tumor cells with greater affinity. Therefore, TEM allows determining whether mouse ATF- or ScFv EGFR targeted IO nanoparticles can be internalized into tumor cells. ATF- or ScFv EGFR targeted IO nanoparticles, or control non-targeted IO nanoparticles can be incubated briefly (about 2 hours) with negative control or positive cells. The cells can then be collected and washed for TEM study following the protocol used previously. If the target specificity is achieved in the tumor cells, IO nanoparticles can be internalized more in the selectively tumor cells, as compared to the negative control cells or cells incubated with non-specific IO nanoparticles.

Figure 13:
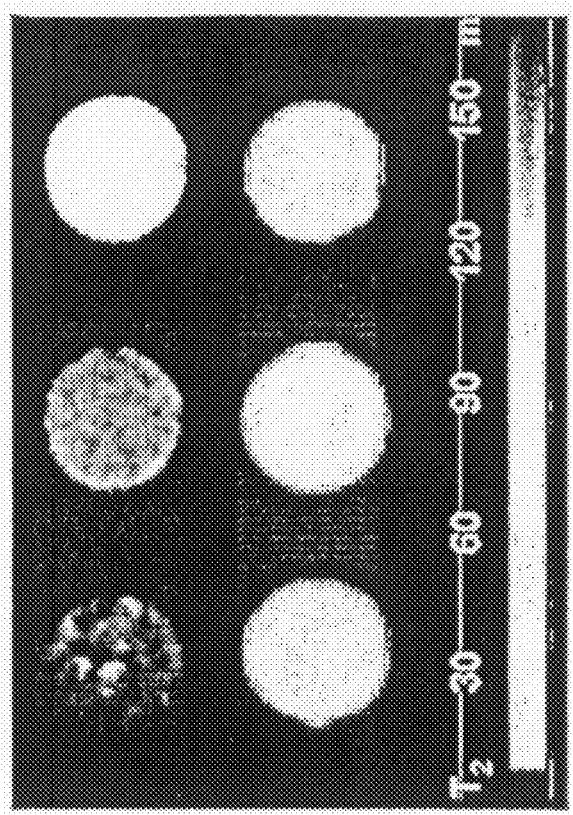
FIG. 13 shows T2 images (top) and $T_2$ maps (low) of a set phantom tubes containing different amount of magnetic nanoparticle labeled cells. The brightest tube contained least amount of labeled cells.

To demonstrate the specific binding and internalization of the targeted-IO particles using MRI, the targeted-IO particles are incubated with the various cell lines in the presence or absence of un-conjugate ATF peptides or ScFv EGFR, which serve as a control for specific receptor-binding. After washing off the unbound contrast agent, the control and positive cells (with different number of cells and cell types) can be suspended and then embedded in soft agar homogeneously in multi-well plates. The sample plate can be then immobilized and scanned using a 3T or 4.7T MR imaging scanner. $T_1$ and $T_2$ weighted spin echo or gradient echo methods are used to obtain $T_2$ dependent images for the samples. $T_2$ value of different samples will be calculated from the images and voxel-by-voxel based on $T_2$ values are plotted out as color-coded image as shown in FIG. 13. The suspension of tumor cells with specific IO probes has altered $T_1$ and shorted $T_1$, $T_2$ and $T^*_2$ values, which can also be visible from MRI images as demonstrated in a previous study [55]. Since $T_2$ value measured by MRI is the function of the iron concentration, the ability of internalization of uPAR and EGFR following the receptor-ligand or antibody binding should increase the intracellular magnetic IO particles and enhance the sensitivity of detecting breast cancer cells. On the other hand, in the presence of un-conjugated targeting peptides, the targeted-IO nanoparticles cannot bind to and be internalized by the cancer cells, which should not alter T1 and short T2 value.

Example 8

Examination of the Feasibility of Adding Both Targeting Peptides and Therapeutic Peptides on a Single QD In one embodiment, a single QD is engineered to have multiple active functional groups for conjugation of targeting and therapeutic peptides. To examine the feasibility of coupling multiple peptides on the QD, an apoptosis-inducing peptide $(KLAKLAK)2$ is used, which is an antibiotic peptide that has been shown to insert to mitochondrial membrane after internalization into cells, resulting in apoptotic cell death [71]. The efficiency of this peptide in treating solid tumors has been demonstrated in several animal tumor models [72, 73].

Figure 14:
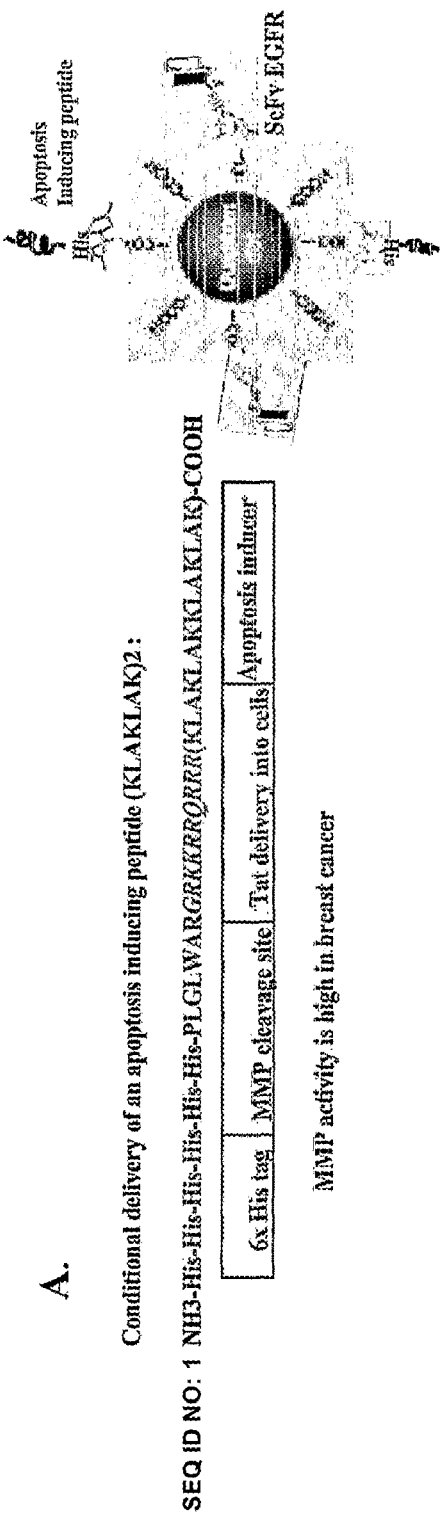
FIG. 14 shows a procedure of conjugation of both targeting and therapeutic peptides on the same QD nanoparticle. (A) Schematic illustration of a conditional releasing apoptosis-inducing peptide. (SEQ ID NO. 1). N-terminal six His: for coupling to QD through Ni-NTA; Common MMP cleavage site (PLGLWAR): cleaved by a high MMP activity in the tumor sites to release the transmembrane domain of HIV Tat; Tat brings apoptosis-inducing peptide (KLAKLAIKLAK-LAK) into tumor cells and induces apoptosis. Both the targeting single chain antibody ScFv EGFR and apoptosis-inducing peptide can be conjugated to the QD simultaneously. (B) Incubation of the conditional releasing peptides with mouse mammary tumor or human breast cancer MCF-7 cells induces a high percentage of apoptotic cell death within 24 hrs.
Figure 14:
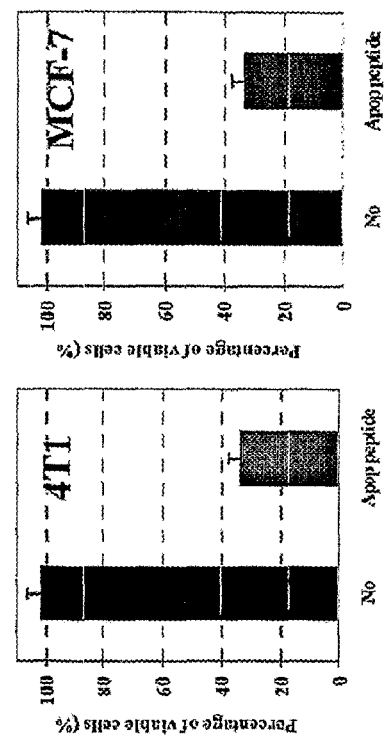

A conditional releasing $(KLAKLAK)_2$ peptide is designed, which includes an MMP cleavage site recognized by all common MMPs, an HIV Tat transmembrane domain for delivery of the peptide into cells, and $(KLAKLAK)2$ for apoptosis induction as shown FIG. 14A. (SEQ ID No. 1) When the peptides are linked to a large particle, such as QDs, it cannot enter into cells. However, in tumor areas, the presence of a high level of MMP activity will cleave the MMP site, thus releasing the Tat and apoptosis inducing peptide domains. Tat can then bring $(KAKKLAK)2$ into cells and induce apoptosis. In the case that the apoptosis-inducing peptides are carried into the cells by the targeted nanoparticles, a high MMP activity inside tumor cells should also cleave the peptide, allowing the $(KAKKLAK)2$ peptide to induce apoptosis. The conditional releasing apoptosis peptide is synthesized t and have already shown that this peptide is able to induce apoptotic cell death in 4T1 and MCF-7 breast cancer cells, as shown in FIG. 16B.

First, 6×His-tagged apoptosis-inducing peptide (for example, Apop peptide) is synthesized. In this case, the six-his tag is located at the N-terminal of the peptide, which is coupled to QDs and prevents non-specific internalization mediated. Then both ScFv EGFR and Apop peptides are conjugated to QDs with —COOH functional groups by mixing both peptides at different ratios. To achieve efficient apoptosis induction, a ratio of ScFv EGFR: Apop peptide around 1:25 to 1:40 may be needed. It is then determined whether the QDs with both targeting and therapeutic peptides are able to bind specifically to tumor cells expressing a high level of EGFR while also inducing apoptotic cell death in those cells, and determine which peptide ratio works best. The breast cancer MDA-MB-231 (EGFR+) and MDA-MB-435 (EGFR−) with QDs conjugated with Apop peptide and ScFv EGFR, with Apop peptide alone or ScFV EGFR-alone, or Non-conjugated QDs are incubated. After 1 to 4 hours of incubation, the cells are examined under an inverted fluorescence microscope to determine whether QDs conjugated with both ScFv EGFR and Apop peptide are able to bind specifically to the MDA-MB-231 cells, but not MDA-MB-435 cells. After 24 hours of incubation, the percentage of viable cells in each treatment group will be measured by a MTS cell proliferation assay to determine if incubation of QDs with both ScFv EGFR and apoptosis-inducing peptides does selectively induce apoptotic cell death in the MDA-MB-231 cells, but not in MDA-Mb-435 cells.

Thus, the present invention, among other things, discloses methods to conjugate quantum dot (QD) nanoparticles to His-tagged targeting peptides or proteins. The His-tagged amino-terminal fragment (ATF) of mouse uPA and the human EGFR single chain antibody (ScFv EGFR) were produced in a bacteria-expression system and then conjugated to QDs through a Ni-NTA chelating compound. The ATF- or ScFv EGFR-QDs bind specifically to cancer cells expressing uPAR or EQGFR respectively, but not to normal cell lines. Systemic delivery of the ATF-QDs targeted the QDs to metastatic lesions in the lung, in a mouse mammary tumor model. Experimental conditions for in vivo tumor imaging of animal tumor models with an optical imaging system has been established e. In addition, a superparamagnetic iron oxide ($Fe_3O_4$) nanocrystal (IO) is synthesized that are stable and can be used in the physiological conditions, for further engineering targeted IO nanoparticles. The conditions for tumor imaging in the mouse using MRI have also been established.

The effects that blocking uPAR with ATF peptides has on both tumor growth and angiogenesis have been examined. The results show that overexpression of mouse or human ATF peptides with adenoviral vectors inhibits tumor growth and decreases tumor vessel density in vivo, in two animal models. Therefore, The ATF peptide is a good candidate for the engineering of dual-function nanoparticles that can be used for in vivo tumor imaging and for anticancer therapy.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

List Of References:

[1]. Gao X, Cui Y, Levenson R M, Chung L W, Nie S. In vivo cancer targeting and imaging with semiconductor quantum dots. Nat Biotechnol 2004; 22:969-76.

[2]. Harisinghani M G, Barentsz J, Hahn P F, Deserno W M, Tabatabaei S, van de Kaa C H, de la Rosette J, Weissleder R. Noninvasive detection of clinically occult lymph-node metastases in prostate cancer. N Engl J Med 2003; 348: 2491-9.

[3]. Hood J D, Bednarski M, Frausto R, Guccione S, Reisfeld R A, Xiang R, Cheresh D A. Tumor regression by targeted gene delivery to the neovasculature. Science 2002; 296: 2404-7.

[4]. Kumar N A, Schnall M D. MR imaging: its current and potential utility in the diagnosis and management of breast cancer. Magn Reson Imaging Clin N Am 2000; 8:715-28.

[5]. Bombardieri E, Crippa F. PET imaging in breast cancer. Q J Nucl Med 2001; 45:245-56.

[6]. Romer J, Nielsen B S, Ploug M. The urokinase receptor as a potential target in cancer therapy. Curr Pharm Des 2004; 10:2359-76.

[7]. Artemov D, Mori N, Ravi R, Bhujwalla Z M. Magnetic resonance molecular imaging of the HER-2/neu receptor. Cancer Res 2003; 63:2723-7.

[8]. Bander N H, Trabulsi E J, Kostakoglu L, Yao D, Vallabhajosula S, Smith-Jones P, Joyce M A, Milowsky M, Nanus D M, Goldsmith S J. Targeting metastatic prostate cancer with radiolabeled monoclonal antibody J591 to the extracellular domain of prostate specific membrane antigen. J Urol 2003; 170:1717-21.

[9]. Moon W K, Lin Y, O'Loughlin T, Tang Y, Kim D E, Weissleder R, Tung C H. Enhanced tumor detection using a folate receptor-targeted near-infrared fluorochrome conjugate. Bioconjug Chem 2003; 14:539-45.

[10]. Mahmood U, Weissleder R. Near-infrared optical imaging of proteases in cancer. Mol Cancer Ther 2003; 2:489-96.

[11]. Schirner M, Menrad A, Stephens A, Frenzel T, Hauff P, Licha K. Molecular imaging of tumor angiogenesis. Ann N Y Acad Sci 2004; 1014:67-75.

[12]. Brigger I, Dubernet C, Couvreur P. Nanoparticles in cancer therapy and diagnosis. Adv Drug Deliv Rev 2002; 54:631-51.

[13]. Brannon-Peppas L, Blanchette J O. Nanoparticle and targeted systems for cancer therapy. Adv Drug Deliv Rev 2004; 56:1649-59.

[14]. Hallahan D, Geng L, Qu S, Scarfone C, Giorgio T, Donnelly E, Gao X, Clanton J. Integrin-mediated targeting of drug delivery to irradiated tumor blood vessels. Cancer Cell 2003; 3:63-74.

[15]. Jain R K. Delivery of molecular and cellular medicine to solid tumors. Adv Drug Deliv Rev 1997; 26:71-90.

[16]. Padera T P, Stoll B R, Tooredman J B, Capen D, di Tomaso E, Jain R K. Pathology: cancer cells compress intratumour vessels. Nature 2004; 427:695.

[17]. Jain R K. Transport of molecules, particles, and cells in solid tumors. Annu Rev Biomed Eng 1999; 1:241-63.

[18]. Hanahan D, Weinberg R A. The hallmarks of cancer. Cell 2000; 100:57-70.

[19]. Behrendt N. The urokinase receptor (uPAR) and the uPAR-associated protein (uPARAP/Endo180): membrane proteins engaged in matrix turnover during tissue remodeling. Biol Chem 2004; 385:103-36.

[20]. Rabbani S A, Mazar A P. The role of the plasminogen activation system in angiogenesis and metastasis. Surg Oncol Clin N Am 2001; 10:393-415, x.

[21]. Liu D, Aguirre Ghiso J, Estrada Y, Ossowski L. EGFR is a transducer of the urokinase receptor initiated signal that is required for in vivo growth of a human carcinoma. Cancer Cell 2002; 1:445-57.

[22]. Carriero M V, Del Vecchio S, Capozzoli M, Franco P, Fontana L, Zannetti A, Botti G, D'Aiuto G, Salvatore M, Stoppelli M P. Urokinase receptor interacts with alpha(v) beta5 vitronectin receptor, promoting urokinase-dependent cell migration in breast cancer. Cancer Res 1999; 59:5307-14.

[23]. Hemsen A, Riethdorf L, Brunner N, Berger J, Ebel S, Thomssen C, Janicke F, Pantel K. Comparative evaluation of urokinase-type plasminogen activator receptor expression in primary breast carcinomas and on metastatic tumor cells. Int J Cancer 2003; 107:903-9.

[24]. Meijer-van Gelder M E, Look M P, Peters H A, Schmitt M, Brunner N, Harbeck N, Klijn J G, Foekens J A. Urokinase-type plasminogen activator system in breast cancer: association with tamoxifen therapy in recurrent disease. Cancer Res 2004; 64:4563-8.

[25]. Solberg H, Ploug M, Hoyer-Hansen G, Nielsen B S, Lund L R. The murine receptor for urokinase-type plasminogen activator is primarily expressed in tissues actively undergoing remodeling. J Histochem Cytochem 2001; 49:237-46.

[26]. Dear A E, Medcalf R L. The urokinase-type-plasminogen-activator receptor (CD87) is a pleiotropic molecule. Eur J Biochem 1998; 252:185-93.

[27]. Li H, Lu H, Griscelli F, Opolon P, Sun L Q, Ragot T, Legrand Y, Belin D, Soria J, Soria C, Perricaudet M, Yeh P. Adenovirus-mediated delivery of a uPA/uPAR antagonist suppresses angiogenesis-dependent tumor growth and dissemination in mice. Gene Ther 1998; 5:1105-13.

[28]. Ignar D M, Andrews J L, Witherspoon S M, Leray J D, Clay W C, Kilpatrick K, Onori J, Kost T, Emerson D L. Inhibition of establishment of primary and micrometastatic tumors by a urokinase plasminogen activator receptor antagonist. Clin Exp Metastasis 1998; 16:9-20.

[29]. Harris R C, Chung E, Coffey R J. EGF receptor ligands. Exp Cell Res 2003; 284:2-13.

[30]. Mendelsohn J. Targeting the epidermal growth factor receptor for cancer therapy. J Clin Oncol 2002; 20:1 S-13S.

[31]. Arteaga C L, Baselga J. Tyrosine kinase inhibitors: why does the current process of clinical development not apply to them? Cancer Cell 2004; 5:525-31.

[32]. Dancey J E. Predictive factors for epidermal growth factor receptor inhibitors—the bull's-eye hits the arrow. Cancer Cell 2004; 5:411-5.

[33]. Arteaga C L, Truica C I. Challenges in the development of anti-epidermal growth factor receptor therapies in breast cancer. Semin Oncol 2004; 31:3-8.

[34]. Aziz S A, Pervez S, Khan S, Kayani N, Rahbar M H. Epidermal growth factor receptor (EGFR) as a prognostic marker: an immunohistochemical study on 315 consecutive breast carcinoma patients. J Pak Med Assoc 2002; 52:104-10.

[35]. Wikstrand C J, McLendon R E, Friedman A H, Bigner D D. Cell surface localization and density of the tumor-associated variant of the epidermal growth factor receptor, EGFRvIII. Cancer Res 1997; 57:4130-40.

[36]. Tsutsui S, Ohno S, Murakami S, Hachitanda Y, Oda S. Prognostic value of epidermal growth factor receptor (EGFR) and its relationship to the estrogen receptor status in 1029 patients with breast cancer. Breast Cancer Res Treat 2002; 71:67-75.

[37]. Nicholson R I, Gee J M, Harper M E. EGFR and cancer prognosis. Eur J Cancer 2001; 37 Suppl 4:S9-15.

[38]. Albanell J, Codony J, Rovira A, Mellado B, Gascon P. Mechanism of action of anti-HER2 monoclonal antibodies: scientific update on trastuzumab and 2C4. Adv Exp Med Biol 2003; 532:253-68.

[39]. Solbach C, Roller M, Ahr A, Loibl S, Nicoletti M, Stegmueller M, Kreysch H G, Knecht R, Kaufmann M. Anti-epidermal growth factor receptor-antibody therapy for treatment of breast cancer. Int J Cancer 2002; 101:390-4.

[40]. Kim E S, Khuri F R, Herbst R S. Epidermal growth factor receptor biology (14C-C225). Curr Opin Oncol 2001; 13:506-13.

[41]. Adams G P, Schier R, McCall A M, Simmons F I, Horak E M, Alpaugh R K, Marks J D, Weiner L M. High affinity restricts the localization and tumor penetration of single-chain fv antibody molecules. Cancer Res 2001; 61:4750-5.

[42]. Bruell D, Bruns C J, Yezhelyev M, Huhn M, Muller J, Ischenko I, Fischer R, Finnern R, Jauch K W, Barth S. Recombinant anti-EGFR immunotoxin 425(scFv)-ETA' demonstrates anti-tumor activity against disseminated human pancreatic cancer in nude mice. Int J Mol Med 2005; 15:305-13.

[43]. Jannot C B, Beerli R R, Mason S, Gullick W J, Hynes N E. Intracellular expression of a single-chain antibody directed to the EGFR leads to growth inhibition of tumor cells. Oncogene 1996; 13:275-82.

[44]. Shinkai M, Ito A. Functional magnetic particles for medical application. Adv Biochem Eng Biotechnol 2004; 91:191-220.

[45]. Bulte J W, Kraitchman D L. Iron oxide MR contrast agents for molecular and cellular imaging. NMR Biomed 2004; 17:484-99.

[46]. Akerman M E, Chan W C, Laakkonen P, Bhatia S N, Ruoslahti E. Nanocrystal targeting in vivo. Proc Natl Acad Sci USA 2002; 99:12617-21.

[47]. Rusckowski M, Qu T, Chang F, Hnatowich D J. Technetium-99m labeled epidermal growth factor-tumor imaging in mice. J Pept Res 1997; 50:393-401.

[48]. Gao X, Nie S. Quantum dot-encoded mesoporous beads with high brightness and uniformity: rapid readout using flow cytometry. Anal Chem 2004; 76:2406-10.

[49]. Bailey R E, Nie S. Alloyed semiconductor quantum dots: tuning the optical properties without changing the particle size. J Am Chem Soc 2003; 125:7100-6.

[50]. Kim S, Lim Y T, Soltesz E G, De Grand A M, Lee J, Nakayama A, Parker J A, Mihaljevic T, Laurence R G, Dor D M, Cohn L H, Bawendi M G, Frangioni J V. Near-infrared fluorescent type II quantum dots for sentinel lymph node mapping. Nat Biotechnol 2004; 22:93-7.

[51]. Chen X, Conti P S, Moats R A. In vivo near-infrared fluorescence imaging of integrin alphavbeta3 in brain tumor xenografts. Cancer Res 2004; 64:8009-14.

[52]. Law B, Curino A, Bugge T H, Weissleder R, Tung C H. Design, synthesis, and characterization of urokinase plasminogen-activator-sensitive near-infrared reporter. Chem Biol 2004; 11:99-106.

[53]. Soltesz E G, Kim S, Laurence R G, DeGrand A M, Parungo C P, Dor D M, Cohn L H, Bawendi M G, Frangioni J V, Mihaijevic T. Intraoperative sentinel lymph node mapping of the lung using near-infrared fluorescent quantum dots. Ann Thorac Surg 2005; 79:269-77; discussion 269-77.

[54]. Gupta A K, Gupta M. Synthesis and surface engineering of iron oxide nanoparticles for biomedical applications. Biomaterials 2005; 26:3995-4021.

[55]. Sundstrom J B, Mao H, Santoianni R, Villinger F, Little D M, Huynh T T, Mayne A E, Hao E, Ansari A A. Magnetic resonance imaging of activated proliferating rhesus macaque T cells labeled with superparamagnetic monocrystalline iron oxide nanoparticles. J Acquir Immune Defic Syndr 2004; 35:9-21.

[56]. Funovics M A, Kapeller B, Hoeller C, Su H S, Kunstfeld R, Puig S, Macfelda K. MR imaging of the her2/neu and 9.2.27 tumor antigens using immunospecific contrast agents. Magn Reson Imaging 2004; 22:843-50.

[57]. Josephson L, Kircher M F, Mahmood U, Tang Y, Weissleder R. Near-infrared fluorescent nanoparticles as combined MR/optical imaging probes. Bioconjug Chem 2002; 13:554-60.

[58]. Kobayashi H, Brechbiel M W. Dendrimer-based nanosized MRI contrast agents. Curr Pharm Biotechnol 2004; 5:539-49.

[59]. Artemov D, Mori N, Okollie B, Bhujwalla Z M. MR molecular imaging of the Her-2/neu receptor in breast cancer cells using targeted iron oxide nanoparticles. Magn Reson Med 2003; 49:403-8.

[60]. Wang Y A, Li J J, Chen H. Peng X. Stabilization of inorganic nanocrystals by organic dendrons. J Am Chem Soc 2002; 124:2293-8.

[61]. Guo W, Li J J, Wang Y A, Peng X. Luminescent CdSe/CdS core/shell nanocrystals in dendron boxes: superior chemical, photochemical and thermal stability. J Am Chem Soc 2003; 125:3901-9.

[62]. Schmitt J, Hess H, Stunnenberg HG. Affinity purification of histidine-tagged proteins. Mol Biol Rep 1993; 18:223-30.

[63]. Hainfeld J F, Liu W, Halsey C M, Freimuth P, Powell R D. Ni-NTA-gold clusters target His-tagged proteins. J Struct Biol 1999; 127:185-98.

[64]. Arbiser J L, Bingaman A, Durham M, Cowan S, Cohen C, Zarnegar E, Varma V, Larsen C P. SVR angiosarcomas can be rejected by CD4 costimulation dependent and CD8 costimulation independent pathways. Mol Med 2002; 8:551-8.

[65]. Aslakson C J, Miller F R. Selective events in the metastatic process defined by analysis of the sequential dissemination of subpopulations of a mouse mammary tumor. Cancer Res 1992; 52:1399-405.

[66]. Newkome G R, Childs B J, Rourk M J, Baker G R, Moorefield C N. Dendrimer construction and macromolecular property modification via combinatorial methods. Biotechnol Bioeng 1998; 61:243-53.

[67]. Sorkin A. Internalization of the epidermal growth factor receptor: role in signalling. Biochem Soc Trans 2001; 29:480-4.

[68]. Rajagopal V, Kreitman R J. Recombinant toxins that bind to the urokinase receptor are cytotoxic without requiring binding to the alpha(2)-macroglobulin receptor. J Biol Chem 2000; 275:7566-73.

[69]. Vilhardt F, Nielsen M, Sandvig K, van Deurs B. Urokinase-type plasminogen activator receptor is internalized by different mechanisms in polarized and nonpolarized Madin-Darby canine kidney epithelial cells. Mol Biol Cell 1999; 10:179-95.

[70]. Li Y, Wood N, Yellowlees D, Donnelly P K. Cell surface expression of urokinase receptor in normal mammary epithelial cells and breast cancer cell lines. Anticancer Res 1999; 19:1223-8.

[71]. Ellerby H M, Arap W, Ellerby L M, Kain R, Andrusiak R, Rio G D, Krajewski S, Lombardo C R, Rao R, Ruoslahti E, Bredesen D E, Pasqualini R. Anti-cancer activity of targeted pro-apoptotic peptides. Nat Med 1999; 5:1032-8.

[72]. Arap W, Haedicke W, Bernasconi M, Kain R, Rajotte D, Krajewski S, Ellerby H M, Bredesen D E, Pasqualini R, Ruoslahti E. Targeting the prostate for destruction through a vascular address. Proc Natl Acad Sci USA 2002; 99:1527-31.

[73]. Mai J C, Mi Z, Kim S H, Ng B, Robbins PD. A proapoptotic peptide for the treatment of solid tumors. Cancer Res 2001; 61:7709-12.

[74]. Soling A, Rainov N G. Bioluminescence imaging in vivo—application to cancer research. Expert Opin Biol Ther 2003; 3:1163-72.

[75]. Kizaka-Kondoh S, Inoue M, Harada H, Hiraoka M. Tumor hypoxia: A target for selective cancer therapy. Cancer Sci 2003; 94:1021-8.

[76]. Dewerchin M, Nuffelen A V, Wallays G, Bouche A, Moons L, Carmeliet P, Mulligan R C, Collen D. Generation and characterization of urokinase receptor-deficient mice. J Clin Invest 1996; 97:870-8.

[77]. Frank J A, Miller B R, Arbab A S, Zywicke H A, Jordan E K, Lewis B K, Bryant L H, Jr., Bulte J W. Clinically applicable labeling of mammalian and stem cells by combining superparamagnetic iron oxides and transfection agents. Radiology 2003; 228:480-7.

[78]. Oca-Cossio J, Mao H, Khokhlova N, Kennedy C M, Kennedy J W, Stabler C L, Hao E, Sambanis A, Simpson N E, Constantinidis I. Magnetically labeled insulin-secreting cells. Biochem Biophys Res Commun 2004; 319:569-75.

[79]. Derfus, A M, Chan, W C W, Bhatia, S N. Probing cytotoxcity of semiconductor quantum dots. Nato Letters 4, 11-18, 2004.

What is claimed is:

1. A nanostructure, comprising:
   a. a quantum dot (QD);
   b. a hydrophobic protection structure including at least one compound selected from a capping ligand, an amphiphilic copolymer, and combinations thereof, wherein the hydrophobic protection structure encapsulates the QD; and
   c. at least one histidine-tagged peptide or at least one histidine-tagged protein, conjugated to the hydrophobic protection structure, wherein the at least one histidine-tagged peptide or protein has at least one binding site.

2. The nanostructure of claim 1, wherein the amphiphilic copolymer is selected from amphiphilic block copolymers, amphiphilic random copolymers, amphiphilic alternating copolymers, amphiphilic periodic copolymers, and combinations thereof.

3. The nanostructure of claim 1, wherein the amphiphilic copolymer is a block copolymer selected from a diblock copolymer, a triblock copolymer, and combinations thereof.

4. The nanostructure of claim 3, wherein the amphiphilic block copolymer includes an ABC triblock structure having grafted 8-carbon alkyl side chains.

5. The nanostructure of claim 4, wherein the ABC triblock structure includes a poly-butylacrylate segment, a poly-ethylacrylate segment, and a poly-methacrylic acid segment.

6. The nanostructure of claim 1, wherein the amphiphilic copolymer has a molecular weight of about 50,000 Da to 200,000 Da, preferably about 100,000 Da.

7. The nanostructure of claim 1, wherein the quantum dot comprises a core and a cap.

8. The nanostructure of claim 7, wherein the core of the quantum dot is selected from the group consisting of IIA-VIA semiconductors, IIIA-VA semiconductors, IVA-IVA semiconductors, and IVA-VIA semiconductors.

9. The nanostructure of claim 7, wherein the core of the quantum dot is selected from the group consisting of IIA-VIA semiconductors.

10. The nanostructure of claim 7, wherein the core of the quantum dot is CdSe.

11. The nanostructure of claim 7, wherein the cap is selected from the group consisting of IIA-VIA semiconductors of high band gap.

12. The nanostructure of claim 7, wherein the cap is selected from ZnS.

13. The nanostructure of claim 1, further comprising a bio-compatibility compound substantially disposed on the hydrophobic protection structure.

14. The nanostructure of claim 13, wherein the bio-compatibility compound is a polyethylene glycol molecule having a molecular weight of about 500 Da to 50,000 Da.

15. The nanostructure of claim 1, further comprising a probe disposed on the hydrophobic protection structure, wherein the probe is selected from an antibody, a polypeptide, a polynucleotide, a drug molecule, an inhibitor compound, and combinations thereof.

16. The nanostructure of claim 1, wherein the capping ligand includes tri-octylphosphine oxide.

17. The nanostructure of claim 1, further comprising a chelating compound for conjugating the at least one histidine-tagged peptide or protein to the hydrophobic protection structure by forming two or more coordinating bonding with the at least one histidine-tagged peptide or protein and the hydrophobic protection structure, respectively.

18. The nanostructure of claim 17, wherein the chelating compound comprises nickel-nitrilotriacetic acid (Ni-NTA).

19. The nanostructure of claim 1, wherein the at least one histidine-tagged peptide or protein comprises a histidine-tagged amino-terminal fragment (ATF) of urokinase plasminogen activator (uPA).

20. The nanostructure of claim 1, wherein the binding site of the at least one histidine-tagged peptide or protein can be at the C-terminal, N-terminal or inside of the peptide or protein between two functional domains on the peptide or protein.

* * * * *

UNITED STATES PATENT AND TRADEMARK OFFICE
CERTIFICATE OF CORRECTION

PATENT NO. : 8,394,760 B2  Page 1 of 1
APPLICATION NO. : 11/919681
DATED : March 12, 2013
INVENTOR(S) : Yang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1404 days.

Signed and Sealed this
First Day of September, 2015

Michelle K. Lee
*Director of the United States Patent and Trademark Office*

SEQUENCE LISTING

```
<160> NUMBER OF SEQ ID NOS: 1

<210> SEQ ID NO 1
<211> LENGTH: 37
<212> TYPE: PRT
<213> ORGANISM: Artificial Sequence
<220> FEATURE:
<223> OTHER INFORMATION: Apoptosis-Inducing peptide with His-tag, MMP
      cleavage site and HIV Tat Transmembrane Domain
<220> FEATURE:
<221> NAME/KEY: SITE
<222> LOCATION: (24)..(37)
```

```
<223> OTHER INFORMATION: Apoptosis-Inducing peptide

<400> SEQUENCE: 1

His His His His His His Pro Leu Gly Leu Trp Ala Arg Gly Arg Lys
1               5                   10                  15

Lys Arg Arg Gln Arg Arg Arg Lys Leu Ala Lys Leu Ala Lys Lys Leu
                20                  25                  30

Ala Lys Leu Ala Lys
            35
```